United States Patent
Hart et al.

(10) Patent No.: US 9,724,125 B2
(45) Date of Patent: Aug. 8, 2017

(54) HIGHLY RESPONSIVE INSTRUMENT SEAL

(71) Applicant: Applied Medical Resources Corporation, Rancho Santa Margarita, CA (US)

(72) Inventors: Charles C. Hart, Rancho Santa Margarita, CA (US); Jeremy J. Albrecht, Rancho Santa Margarita, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 0 days.

(21) Appl. No.: 15/221,894

(22) Filed: Jul. 28, 2016

(65) Prior Publication Data

US 2016/0331403 A1    Nov. 17, 2016

Related U.S. Application Data

(63) Continuation of application No. 14/931,565, filed on Nov. 3, 2015, now Pat. No. 9,427,257, which is a
(Continued)

(51) Int. Cl.
*A61B 17/34* (2006.01)
*A61M 39/06* (2006.01)
*A61B 17/02* (2006.01)

(52) U.S. Cl.
CPC ...... *A61B 17/3423* (2013.01); *A61B 17/0218* (2013.01); *A61B 17/3462* (2013.01);
(Continued)

(58) Field of Classification Search
CPC ............ A61B 17/3462; A61B 17/3423; A61B 17/3415
See application file for complete search history.

(56) References Cited

U.S. PATENT DOCUMENTS 5,122,122 A * 6/1992 Allgood .............. A61B 17/34
604/105
5,180,373 A * 1/1993 Green ............... A61B 17/3498
251/149.1
(Continued)

OTHER PUBLICATIONS

International Searching Authority—European Patent Office, The International Search Report and Written Opinion for International Application No. PCT/US2015/039582, mailed Sep. 25, 2015.
(Continued)

*Primary Examiner* — Ellen C Hammond
*Assistant Examiner* — Stuart S Bray
(74) *Attorney, Agent, or Firm* — Rimas T. Lukas

(57) ABSTRACT

A surgical access port for passage through body tissue to provide access to an underlying tissue site is provided. The access port has a working channel dimensioned for receiving a surgical instrument and a seal assembly for providing a substantial seal before, during and after insertion of a surgical instrument. The seal assembly includes an instrument seal and a zero seal. The instrument seal includes a proximal base that is interconnected to a distal instrument engaging portion by an elongate supporting portion. The engaging portion has a lateral dimension larger than the lateral dimension of the supporting portion forming a bulbous, mushroom-like head. The lateral dimension of the engaging portion decreases toward a distal opening of the instrument seal such that the distal end of the engaging portion is substantially perpendicular to the seal axis. The supporting portion closely conforms to an inserted instrument and serves to align the distal end of the seal.

17 Claims, 27 Drawing Sheets

Related U.S. Application Data continuation of application No. PCT/US2015/039582, filed on Jul. 8, 2015.

(60) Provisional application No. 62/022,039, filed on Jul. 8, 2014.

(52) U.S. Cl.
CPC ..... *A61M 39/06* (2013.01); *A61B 2017/3441* (2013.01); *A61B 2017/3464* (2013.01)

(56) References Cited

U.S. PATENT DOCUMENTS

| | | | | |
|---|---|---|---|---|
| 5,217,451 A * | 6/1993 | Freitas | ............... | A61B 17/34 604/105 |
| 5,232,451 A * | 8/1993 | Freitas | ............... | A61B 17/34 604/174 |
| 5,330,497 A * | 7/1994 | Freitas | ............... | A61B 17/34 604/164.12 |
| 5,385,553 A * | 1/1995 | Hart | ............... | A61B 17/3462 604/167.03 |
| 5,429,609 A * | 7/1995 | Yoon | ............... | A61B 17/3417 604/167.03 |
| 5,443,452 A | 8/1995 | Hart et al. | | |
| 5,496,280 A * | 3/1996 | Vandenbroek | ..... | A61B 17/3498 604/167.03 |
| 5,545,141 A * | 8/1996 | Eld | ............... | A61B 17/3415 604/170.03 |
| 5,549,566 A * | 8/1996 | Elias | ............... | A61M 39/045 604/167.03 |
| 5,562,688 A * | 10/1996 | Riza | ............... | A61B 17/0469 606/139 |
| 5,603,702 A * | 2/1997 | Smith | ............... | A61B 17/3462 251/149.1 |
| 5,653,718 A * | 8/1997 | Yoon | ............... | A61B 17/34 604/174 |
| 5,709,664 A | 1/1998 | Vandenbroek et al. | | |
| 5,716,369 A * | 2/1998 | Riza | ............... | A61B 17/0469 606/139 |
| 5,720,759 A * | 2/1998 | Green | ............... | A61B 17/3462 604/165.01 |
| 5,727,770 A * | 3/1998 | Dennis | ............... | A61B 17/3462 251/149.1 |
| 5,743,883 A * | 4/1998 | Visconti | ............... | A61M 39/06 251/149.1 |
| 5,803,919 A | 9/1998 | Hart et al. | | |
| 5,840,063 A * | 11/1998 | Flaherty | ............ | A61M 39/0208 604/175 |
| 6,024,725 A * | 2/2000 | Bollinger | ............... | A61M 39/06 604/164.01 |
| 6,258,065 B1 | 7/2001 | Dennis et al. | | |
| 6,860,869 B2 | 3/2005 | Dennis | | |
| 7,056,303 B2 | 6/2006 | Dennis et al. | | |
| 7,083,626 B2 | 8/2006 | Hart et al. | | |
| 7,112,185 B2 | 9/2006 | Hart et al. | | |
| 7,438,702 B2 | 10/2008 | Hart et al. | | |
| 7,473,243 B2 | 1/2009 | Dennis et al. | | |
| 7,585,288 B2 | 9/2009 | Haberland et al. | | |
| 7,632,250 B2 | 12/2009 | Smith et al. | | |
| 7,771,395 B2 | 8/2010 | Hart et al. | | |
| 7,798,991 B2 | 9/2010 | Insignares | | |
| 7,833,199 B2 | 11/2010 | Franer et al. | | |
| 7,918,826 B2 | 4/2011 | Armstrong et al. | | |
| 7,918,827 B2 | 4/2011 | Smith | | |
| 7,931,624 B2 | 4/2011 | Smith et al. | | |
| 7,938,804 B2 | 5/2011 | Fischvogt | | |
| 7,951,118 B2 | 5/2011 | Smith et al. | | |
| 7,981,076 B2 * | 7/2011 | Sullivan | ............... | A61M 5/1409 604/131 |
| 7,988,671 B2 | 8/2011 | Albrecht et al. | | |
| 8,002,750 B2 | 8/2011 | Smith | | |
| 8,075,530 B2 | 12/2011 | Taylor et al. | | |
| 8,118,785 B2 | 2/2012 | Hart et al. | | |
| 8,147,458 B2 | 4/2012 | Hart et al. | | |
| 8,152,773 B2 | 4/2012 | Albrecht et al. | | |
| 8,246,586 B2 | 8/2012 | Schweitzer et al. | | |
| 8,257,315 B2 | 9/2012 | Franer et al. | | |
| 8,257,317 B2 | 9/2012 | Albrecht et al. | | |
| 8,262,623 B2 | 9/2012 | Nijland et al. | | |
| 8,430,851 B2 | 4/2013 | McGinley et al. | | |
| 8,435,174 B2 | 5/2013 | Cropper et al. | | |
| 8,562,569 B2 * | 10/2013 | Hart | ............... | A61B 17/3462 604/108 |
| 8,597,251 B2 | 12/2013 | Albrecht et al. | | |
| 8,613,727 B2 | 12/2013 | Hart et al. | | |
| 8,636,686 B2 | 1/2014 | Minnelli et al. | | |
| 8,684,975 B2 * | 4/2014 | Albrecht | ............... | A61B 17/3421 604/164.01 |
| 8,696,635 B2 | 4/2014 | Smith et al. | | |
| 8,696,636 B2 | 4/2014 | Schweitzer et al. | | |
| 8,968,249 B2 | 3/2015 | Smith et al. | | |
| 8,968,250 B2 | 3/2015 | McGinley et al. | | |
| 2001/0021825 A1 * | 9/2001 | Becker | ............... | A61M 39/06 604/167.01 |
| 2002/0002351 A1 * | 1/2002 | Cote, Sr. | ............... | A61M 39/26 604/247 |
| 2002/0107484 A1 | 8/2002 | Dennis et al. | | |
| 2004/0006330 A1 * | 1/2004 | Fangrow, Jr. | ......... | A61M 39/02 604/533 |
| 2004/0006358 A1 * | 1/2004 | Wulfman | ............... | A61B 5/061 606/167 |
| 2004/0068232 A1 | 4/2004 | Hart et al. | | |
| 2005/0131349 A1 | 6/2005 | Albrecht et al. | | |
| 2005/0143756 A1 | 6/2005 | Jankowski | | |
| 2005/0256455 A1 * | 11/2005 | Weststrate | ......... | A61B 17/3415 604/104 |
| 2005/0261630 A1 * | 11/2005 | Mottola | ............... | A61M 39/02 604/167.04 |
| 2006/0229565 A1 | 10/2006 | Dennis et al. | | |
| 2006/0253077 A1 * | 11/2006 | Smith | ............... | A61B 17/3421 604/167.06 |
| 2007/0027453 A1 | 2/2007 | Hart et al. | | |
| 2007/0088277 A1 | 4/2007 | McGinley et al. | | |
| 2007/0100295 A1 * | 5/2007 | Belley | ............... | A61M 39/06 604/246 |
| 2007/0225647 A1 * | 9/2007 | Luther | ............... | A61M 39/06 604/167.03 |
| 2008/0086080 A1 | 4/2008 | Mastri et al. | | |
| 2008/0108944 A1 * | 5/2008 | Woehr | ............... | A61B 5/1411 604/164.08 |
| 2008/0171988 A1 | 7/2008 | Blanco | | |
| 2008/0249475 A1 | 10/2008 | Albrecht et al. | | |
| 2009/0105635 A1 * | 4/2009 | Bettuchi | ............... | A61B 17/3421 604/26 |
| 2009/0204077 A1 * | 8/2009 | Hasted | ............... | A61M 5/14248 604/240 |
| 2009/0281481 A1 * | 11/2009 | Harding | ............ | A61M 25/0606 604/28 |
| 2010/0004599 A1 * | 1/2010 | Zhou | ............... | A61B 17/3421 604/167.04 |
| 2010/0100045 A1 * | 4/2010 | Pravongviengkham | | A61B 17/3421 604/164.09 |
| 2010/0114033 A1 | 5/2010 | Fischvogt | | |
| 2010/0204648 A1 * | 8/2010 | Stout | ............... | A61M 25/0606 604/122 |
| 2010/0217208 A1 * | 8/2010 | Snow | ............... | A61M 39/06 604/246 |
| 2010/0249694 A1 | 9/2010 | Choi et al. | | |
| 2010/0274193 A1 | 10/2010 | Patton et al. | | |
| 2010/0280456 A1 * | 11/2010 | Nijland | ............... | A61M 39/06 604/167.03 |
| 2011/0036844 A1 * | 2/2011 | Gyrn | ............... | A61M 5/14248 220/361 |
| 2011/0087168 A1 * | 4/2011 | Parihar | ............... | A61B 17/34 604/167.03 |
| 2011/0087169 A1 * | 4/2011 | Parihar | ............... | A61B 17/34 604/167.03 |
| 2011/0124971 A1 | 5/2011 | Ramos et al. | | |

(56) References Cited

U.S. PATENT DOCUMENTS

| | | | |
|---|---|---|---|
| 2011/0144440 A1* | 6/2011 | Cropper | A61B 17/3421 600/203 |
| 2011/0144443 A1* | 6/2011 | Shelton, IV | A61B 1/32 600/206 |
| 2011/0245619 A1 | 10/2011 | Holcomb | |
| 2011/0288483 A1 | 11/2011 | Zhou et al. | |
| 2012/0108889 A1* | 5/2012 | Behan | A61F 2/0009 600/30 |
| 2012/0130391 A1* | 5/2012 | Sundt, III | A61M 1/10 606/108 |
| 2012/0253285 A1 | 10/2012 | Patton et al. | |
| 2012/0323188 A1* | 12/2012 | Yavorsky | A61M 39/06 604/256 |
| 2013/0030372 A1 | 1/2013 | Franer et al. | |
| 2013/0046252 A1* | 2/2013 | Yavorsky | A61M 39/06 604/244 |
| 2013/0046253 A1* | 2/2013 | Yavorsky | A61M 39/06 604/257 |
| 2013/0066281 A1* | 3/2013 | Yavorsky | A61M 39/06 604/257 |
| 2013/0150793 A1* | 6/2013 | Beissel | A61M 25/0105 604/171 |
| 2013/0204095 A1* | 8/2013 | Mark | A61B 17/32001 600/249 |
| 2013/0310773 A1* | 11/2013 | Richard | A61B 17/3462 604/278 |
| 2014/0024899 A1* | 1/2014 | Kleyman | A61B 17/3423 600/204 |
| 2014/0180015 A1* | 6/2014 | Shipp | A61B 17/34 600/204 |
| 2014/0276453 A1* | 9/2014 | Woehr | A61M 25/0618 604/246 |
| 2014/0316350 A1* | 10/2014 | Yamaguchi | A61M 39/06 604/246 |
| 2015/0112271 A1* | 4/2015 | Chelak | A61M 39/06 604/186 |
| 2015/0119855 A1* | 4/2015 | Khalaj | A61M 39/10 604/513 |
| 2015/0141738 A1* | 5/2015 | Toellner | A61M 25/0662 600/16 |
| 2015/0151089 A1* | 6/2015 | Tan | A61M 25/0693 604/508 |
| 2015/0157843 A1* | 6/2015 | Pepin | A61M 25/0097 604/167.04 |
| 2015/0202421 A1* | 7/2015 | Ma | A61M 39/06 604/167.03 |
| 2015/0328445 A1* | 11/2015 | Khalaj | A61M 25/00 604/535 |
| 2015/0342602 A1* | 12/2015 | Jimenez | A61B 17/0401 606/215 |

OTHER PUBLICATIONS

The International Bureau of WIPO, International Preliminary Report on Patentability for International Application No. PCT/US2015/039582, entitled "Highly Responsive Instrument Seal," dated Jan. 19, 2017, 6 pgs.

* cited by examiner

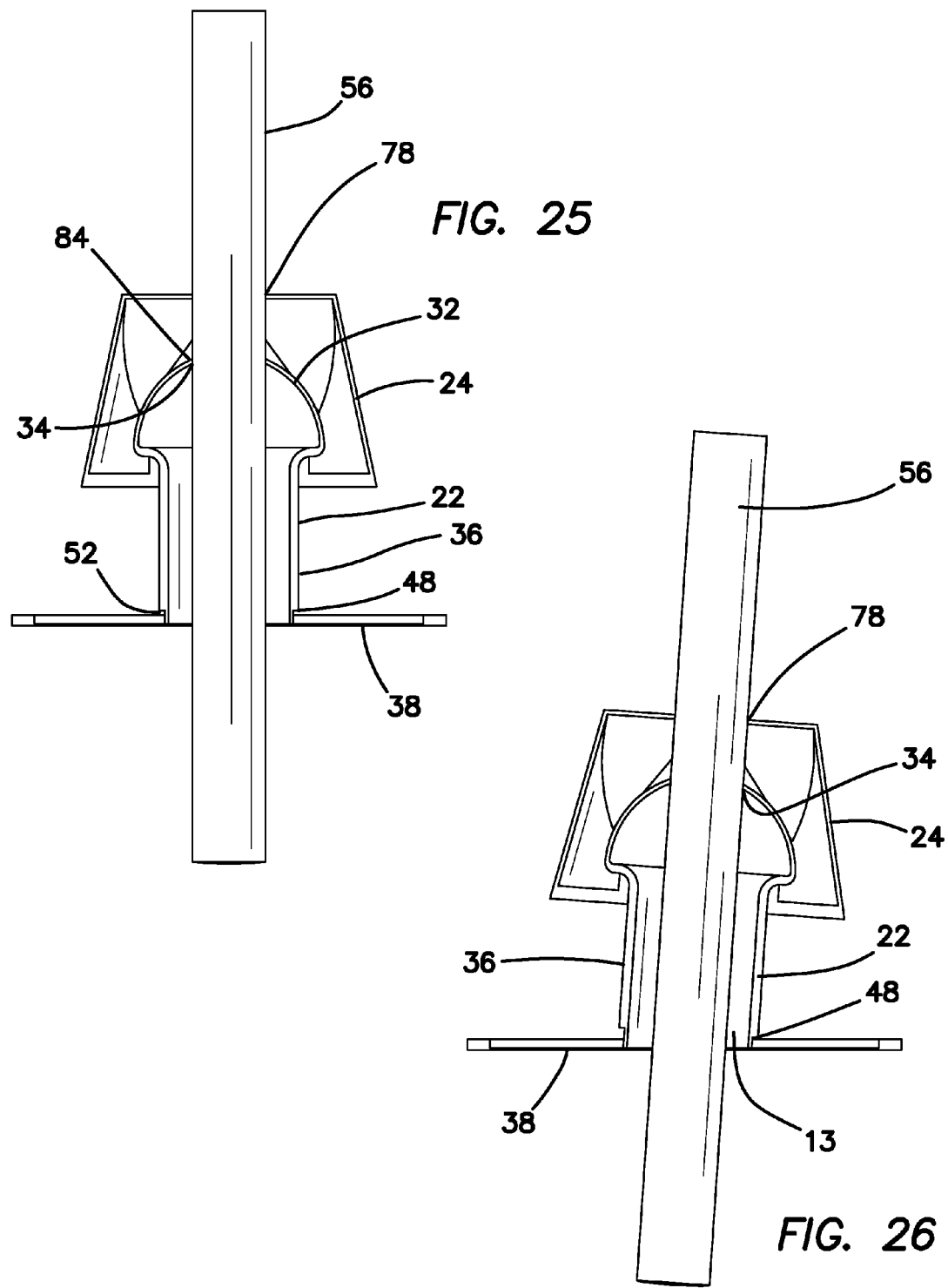

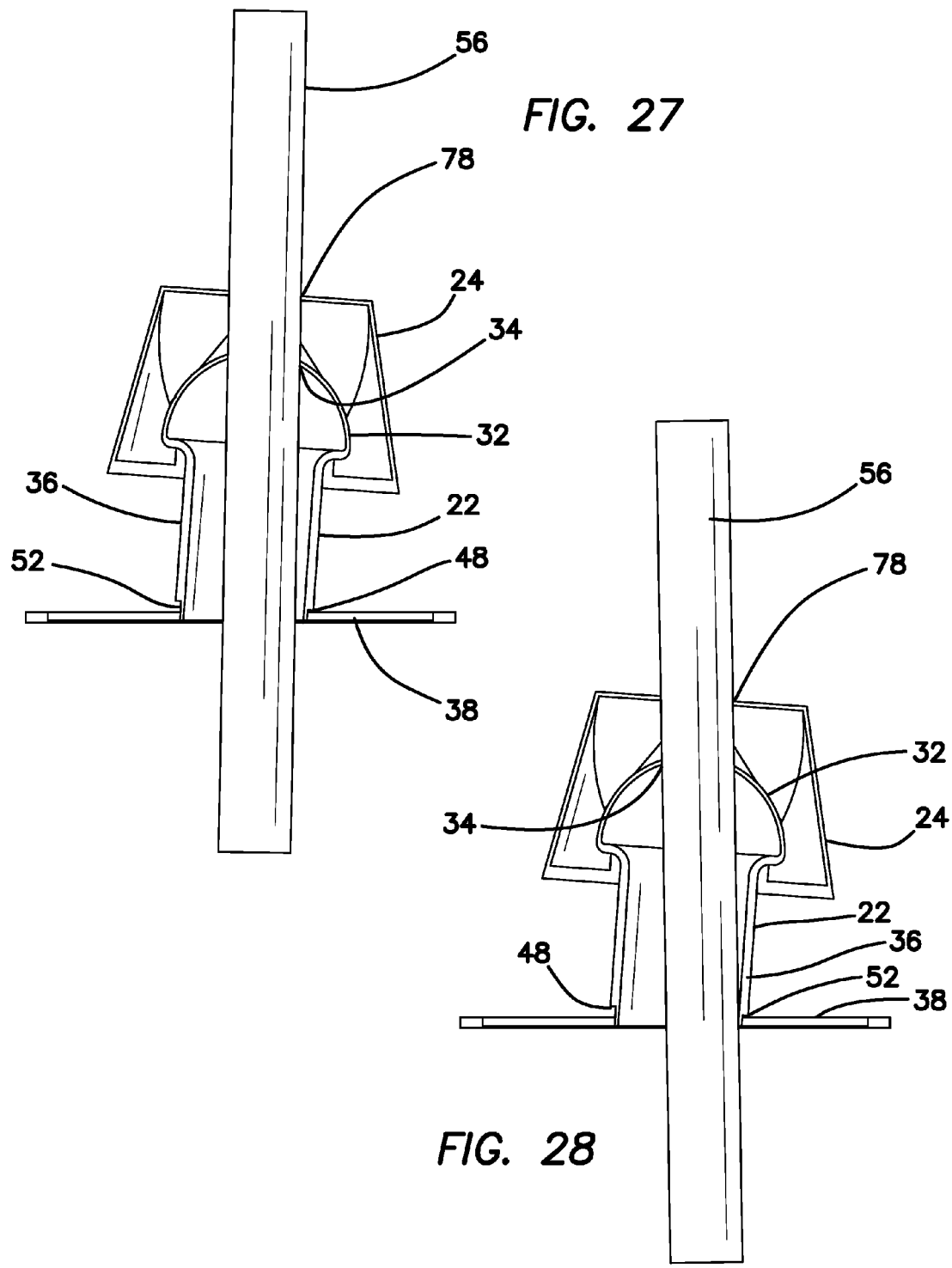

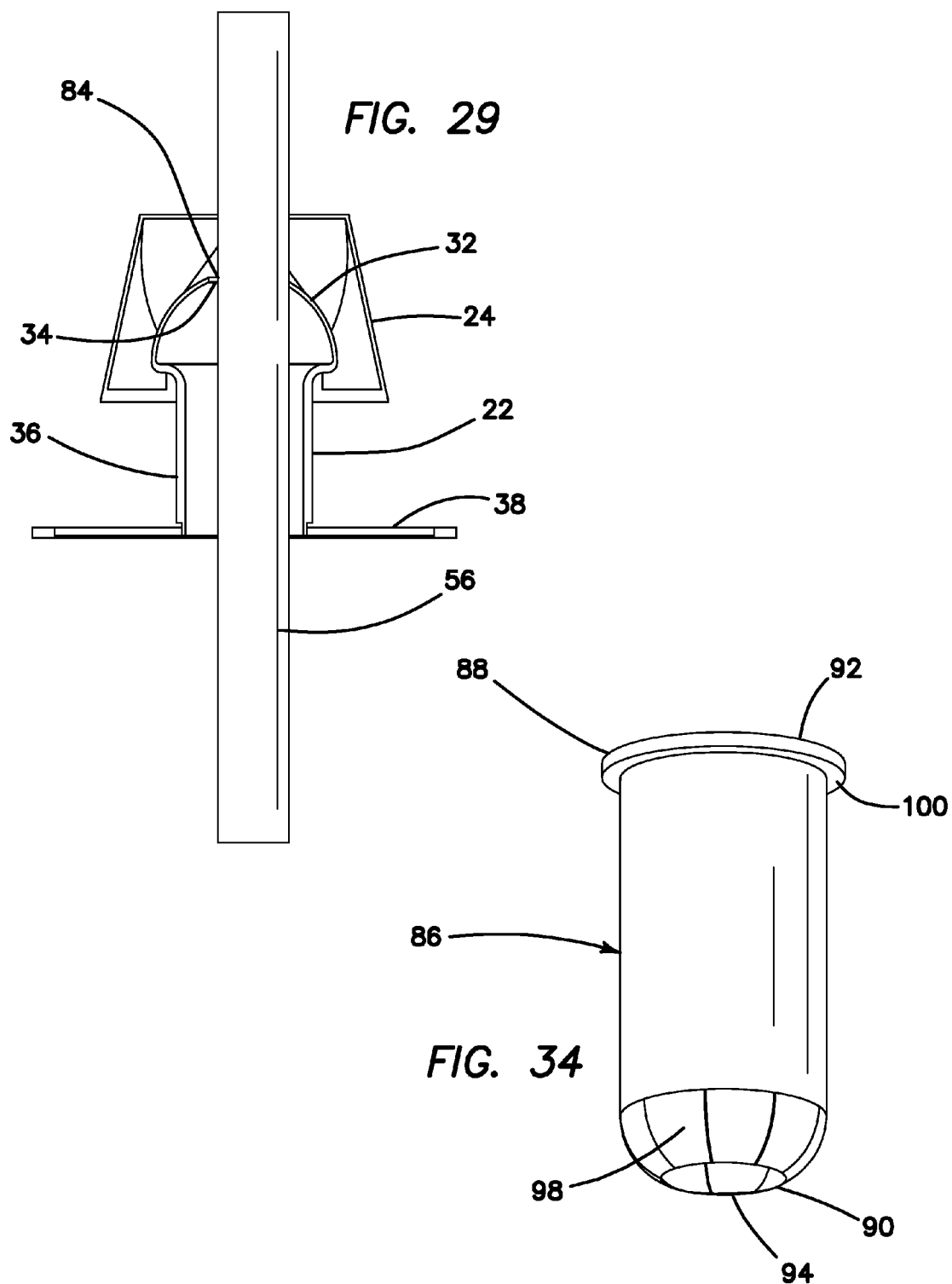

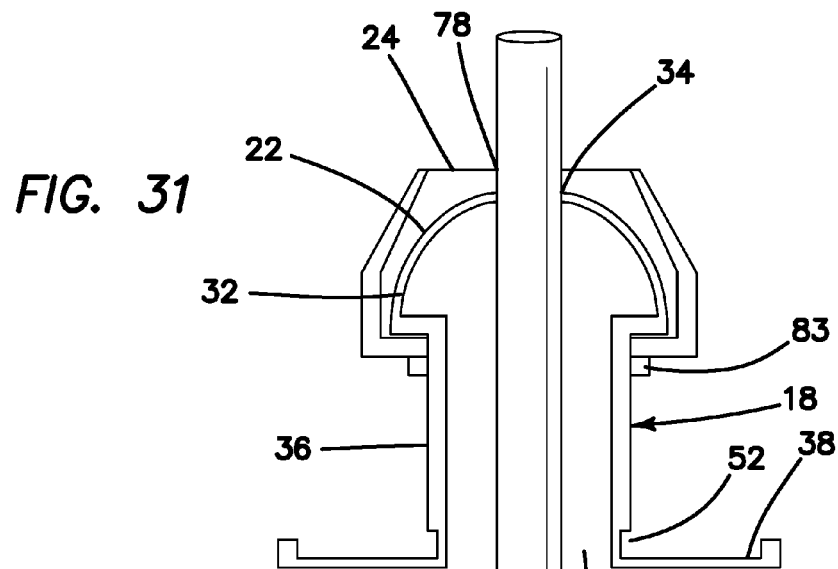
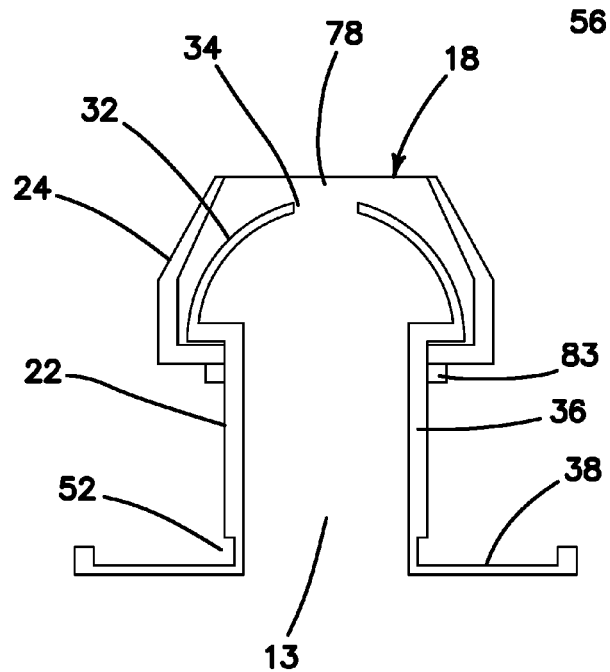
FIG. 31
FIG. 30

HIGHLY RESPONSIVE INSTRUMENT SEAL

CROSS-REFERENCE TO RELATED APPLICATION

This patent application is a continuation of U.S. application Ser. No. 14/931,565 entitled "Highly responsive instrument seal" filed Nov. 3, 2015 incorporated herein by reference in its entirety, which is a continuation of International Application No. PCT/US2015/039582 entitled "Highly responsive instrument seal" filed on Jul. 8, 2015 and incorporated herein by reference in its entirety which claims priority to and benefit of U.S. Provisional Patent Application Ser. No. 62/022,039 entitled "Highly responsive instrument seal" filed on Jul. 8, 2014 which is hereby incorporated by reference in its entirety.

FIELD OF THE INVENTION

This application relates to surgical instruments, and in particular, to surgical access devices such as trocars comprising a seal assembly.

BACKGROUND OF THE INVENTION

Laparoscopic surgery is a type of minimally invasive surgery in which instruments access internal structures of a patient's body through one or more access devices or trocars. In some laparoscopic procedures, a body cavity is inflated or insufflated with an insufflation gas, for example, carbon dioxide, which provides additional room for manipulating the instruments in the body cavity, thereby facilitating the surgical procedure. The term "pneumoperitoneum" refers to an abdominal cavity in an insufflated state. To maintain pneumoperitoneum, trocars are equipped with one or more seals that prevent insufflation gas from escaping as instruments are inserted, withdrawn, and/or manipulated during an operation. These seals typically comprise elastomeric materials and seal circumferentially against an inserted instrument. Usually, a zero seal and an instrument seal are employed within the trocar.

Numerous technical challenges confront those designing and manufacturing seals for trocars. For example, as an instrument is moved with respect to a seal, the seal will rub against the instrument and create friction. Stiction and hysteresis will also arise. Stiction is the static friction of a stationary instrument in contact with a stationary seal that needs to be overcome to enable their relative motion. Elastomeric seal materials elongate when instruments are inserted, thereby increasing drag force. Oil canning, or the inversion or folding over, of typical seals can also result in loss of precise instrument control and movement because the surgeon experiences a different feedback between large and small changes in the position of the instrument. These aspects, including friction, stiction, hysteresis and oil canning, must be minimized if a seal is to be used in very delicate and precise procedures wherein an instrument must be maneuvered accurately without restriction. Examples of seal technology which overcome these problems include U.S. Pat. Nos. 8,684,975, 8,613,727, 8,562,569, 5,385,553 issued to Applied Medical Resources Corporation and incorporated by reference in their entirety herein. These patents provide floating and pendant seals that are configured to follow the motion of an inserted instrument and allow a minimum sealing pressure upon the shaft of an instrument. The present invention provides a new and improved trocar having a seal with significantly reduced friction, stiction, hysteresis and oil canning properties.

SUMMARY OF THE INVENTION

According to one aspect of the invention, a surgical access device having a working channel extending along a longitudinal axis between a proximal end and a distal end is provided. The surgical access device includes a seal housing and a cannula extending distally from the seal housing. The device further includes a seal assembly disposed in mechanical cooperation with the seal housing. The seal assembly includes an instrument seal disposed in the working channel. The instrument seal has a central lumen extending along a central seal axis between a proximal opening at a proximal end of the instrument seal and a distal opening at a distal end of the instrument seal. The proximal opening and the distal opening are coaxial with the seal axis. The instrument seal includes a base portion at the proximal end of the instrument seal defining the proximal opening. The base portion extends circumferentially outwardly from the proximal opening. The central lumen at the base portion has a first diameter. The instrument seal further includes a cylindrical supporting portion extending distally from the base portion along the seal axis. The supporting portion has a proximal end and a distal end. The supporting portion includes an inner surface and an outer surface defining a wall thickness therebetween. The supporting portion has a circular cross-section taken perpendicular to the seal axis. The central lumen at the supporting portion has a second diameter that is constant along the length of the supporting portion. The instrument seal further includes an instrument engaging portion integrally formed with and extending distally from the supporting portion. The instrument engaging portion includes an outer surface and an inner surface defining a partial spherical shape and having a maximum diameter that is larger than the second diameter. The instrument engaging portion defines the distal opening at the distal end of the instrument seal formed in the spherical shape. The distal opening has a distal diameter that is smaller than the second diameter. The base portion is connected to the seal housing such that the distal end of the instrument seal is allowed to pendulate with respect to the seal housing.

According to another aspect of the invention, a surgical access port for passage through body tissue to provide access to an underlying tissue site is provided. The surgical access port includes a working channel extending from a proximal end and a distal end. The working channel is dimensioned for receiving a surgical instrument. The access port further includes a seal assembly for providing a substantial seal before, during and after insertion of a surgical instrument. The seal assembly is disposed in the working channel and includes a seal holder, an instrument seal and a zero seal. The instrument seal includes a proximal base that is interconnected to a distal instrument engaging portion by an elongate supporting portion. The engaging portion has a diameter larger than the diameter of the supporting portion forming a mushroom-like head. The diameter of the engaging portion decreases toward a distal opening of the instrument seal such that the distal end of the engaging portion is substantially perpendicular to a seal axis. The supporting portion closely conforms to an inserted surgical instrument and aligns the distal opening at the distal end of the instrument engaging portion with the inserted instrument before the inserted instrument enters the instrument engaging portion from a proximal opening of the instrument seal.

The proximal opening and the distal opening of the instrument seal are coaxial with the seal axis.

According to another aspect of the invention, a surgical seal assembly for use with a surgical access device having a longitudinal axis is provided. The seal assembly includes a seal holder including a wall portion defining a working channel dimensioned to permit passage of a surgical instrument. The seal assembly includes an instrument seal connected to the seal holder and disposed in the working channel. The instrument seal has a central lumen extending along a central seal axis between a proximal opening at the proximal end of the instrument seal and a distal orifice at a distal end of the instrument seal. The instrument seal includes a base portion at the proximal end of the instrument seal. The base extends laterally outwardly from the proximal opening. The instrument seal includes an elongate throat portion extending distally from the base portion along the seal axis. The throat portion has a throat length along the seal axis between a proximal end and a distal end of the throat portion. The central lumen has a throat diameter that is substantially constant along the length of the throat portion. The instrument seal further includes a head portion extending distally from the distal end of the throat portion. The head portion has a proximal end and a distal end. The head portion defines the distal orifice of the instrument seal at the distal end of the head portion. The distal orifice and the proximal opening are coaxial with the seal axis. The head portion has a head diameter larger than the throat diameter. The head diameter decreases toward the distal orifice. The distal orifice has an orifice diameter that is smaller than the throat diameter. The base portion is connected to the seal holder such that the throat portion pendulates together with the head portion.

According to another aspect of the invention, a surgical seal assembly for use with a surgical access device having a longitudinal axis is provided. The seal assembly includes a seal holder including a wall portion defining a working channel dimensioned to permit passage of a surgical instrument. The seal assembly further includes an instrument seal connected to the seal holder and disposed in the working channel. The instrument seal has a central lumen extending along a central seal axis between a proximal opening at the proximal end of the instrument seal and a distal orifice at a distal end of the instrument seal. The instrument seal includes a base portion at the proximal end of the instrument seal. The base portion extends laterally outwardly from the proximal opening. The instrument seal further includes an elongate throat portion extending distally from the base portion along the seal axis. The throat portion has a throat length along the seal axis between a proximal end and a distal end of the throat portion. The central lumen has a throat diameter that is substantially constant along the length of the throat portion. The throat length is substantially greater than the throat diameter. The instrument seal further includes a head portion extending distally from the distal end of the throat portion. The head portion has a proximal end and a distal end. The head portion defines the distal orifice of the instrument seal at the distal end of the head portion. The distal orifice and the proximal opening are coaxial with the seal axis. The head portion has a head diameter larger than the throat diameter. The head diameter decreases toward the distal orifice. The distal orifice has an orifice diameter that is smaller than the throat diameter. The ratio of the throat diameter to the throat length is approximately 1:2.

According to another aspect of the invention, a surgical access device having a working channel extending along a longitudinal axis between a proximal end and a distal end is provided. The surgical access device includes a seal housing and a cannula extending distally from the seal housing. The device further includes a seal assembly disposed in mechanical cooperation with the seal housing. The seal assembly includes an instrument seal disposed in the working channel. The instrument seal has a central lumen extending along a central seal axis between a proximal opening at a proximal end of the instrument seal and a distal opening at a distal end of the instrument seal. The instrument seal includes a base portion at the proximal end defining the proximal opening. The base portion extends laterally outwardly from the proximal opening. The central lumen at the base portion has a first diameter. The instrument seal further includes an elongate supporting portion extending distally from the base portion along the seal axis. The supporting portion includes an inner surface and an outer surface defining a thickness therebetween. The central lumen at the supporting portion defines a second diameter. The instrument seal further includes an instrument engaging portion having a proximal end and a distal end. The instrument engaging portion extends distally along the seal axis from the supporting portion. The instrument engaging portion defines the distal opening at the distal end of the instrument seal. The distal opening has a distal diameter that is smaller than the second diameter. The instrument engaging portion includes an outer surface and an inner surface defining a curved shape having a third diameter that increases from the second diameter at the proximal end and decreases progressively to the distal diameter. The base portion is fixed to the seal housing such that the supporting portion and instrument engaging portion of the instrument seal are allowed to pendulate relative to the seal housing.

According to another aspect of the invention, a surgical access device having a working channel extending along a longitudinal axis between a proximal end and a distal end dimensioned and adapted for receiving a surgical instrument is provided. The surgical access device includes a seal housing and a cannula extending distally from the seal housing. The surgical access device further includes a seal assembly disposed in the seal housing. The seal assembly is configured to form a seal around an instrument inserted into the working channel at the proximal end and extending through the working channel at the distal end. The seal assembly includes an instrument seal disposed in the working channel. The instrument seal has a central lumen extending along a central seal axis between a proximal opening at a proximal end and a distal opening at a distal end of the instrument seal. The instrument seal includes further includes a base portion defining the proximal opening of the central lumen. The base portion extends laterally outwardly at the proximal opening and has an upper surface and a lower surface defining a thickness therebetween. The instrument seal further includes a cylindrical supporting portion extending distally from the base portion. The cylindrical supporting portion includes an inner surface and an outer surface defining a thickness therebetween. The central lumen has a substantially constant diameter along the central seal axis from a proximal end of the supporting portion to a distal end of the supporting portion. The instrument seal further includes an instrument engaging portion having a proximal end and a distal end. The instrument engaging portion extends distally from the supporting portion. The distal opening of the instrument seal is formed at the distal end of the instrument engaging portion. The distal opening is dimensioned and adapted to seal against an instrument inserted into the instrument seal. The instrument engaging portion has a bulbous shape and has a diameter larger than the diameter of the supporting portion. The instrument engaging portion is curved such that the instrument engaging portion at the distal opening is substantially perpendicular to the central seal axis when in a relaxed undeflected configuration.

According to one aspect of the invention, an instrument seal for use in a surgical access device is provided. The instrument seal includes an instrument engaging portion connected to an elongate support portion that is, in turn, connected to a resilient and responsive base portion.

According to another aspect of the invention, an instrument seal for use in a surgical access device is provided. The instrument seal includes a semi-spherical instrument engaging portion having an orifice sized and configured to provide a gas-tight seal against an inserted instrument. The proximal end of the instrument seal is connected to a rigid or semi-rigid elongate support portion which at its proximal end is connected to a highly resilient base portion; the base portion being more resilient/flexible than the elongate support portion. The surgical access device may further be provided with a zero seal having a distal opening that is distal to the orifice of the instrument seal.

According to another aspect of the invention, an instrument seal for use in a surgical access device is provided. The instrument seal includes a semi-spherical instrument engaging portion having an orifice sized and configured to provide a gas-tight seal against an inserted instrument. The proximal end of the instrument seal is connected to a rigid or semi-rigid elongate support portion that is relatively less flexible/resilient than the instrument engaging portion. The support portion has an appropriate length-to-diameter ratio. The proximal end of support portion is connected to a highly-resilient and/or convoluted base portion. The base portion is more flexible/resilient compared to the support portion and/or has one or more convolutions to provide greater flexibility, resiliency and responsiveness to the instrument seal. The surgical access device may be further provided with a zero seal having a distal opening that is distal to the orifice of the instrument seal.

BRIEF DESCRIPTION OF THE DRAWINGS

FIG. 25 is a cross-sectional, side view of an instrument inserted through an instrument seal and a zero seal according to the present invention.

FIG. 26 is a cross-sectional, side view of an instrument inserted through an instrument seal and a zero seal according to the present invention.

FIG. 27 is a cross-sectional, side view of an instrument inserted through an instrument seal and a zero seal according to the present invention.

FIG. 28 is a cross-sectional, side view of an instrument inserted through an instrument seal and a zero seal according to the present invention.

FIG. 29 is a cross-sectional, side view of an instrument inserted through an instrument seal and a zero seal according to the present invention.

FIG. 30 is a cross-sectional, side view of an instrument seal and a zero seal according to the present invention.

FIG. 31 is a cross-sectional, side view of an instrument inserted through an instrument seal and a zero seal according to the present invention.

FIG. 34 is a top perspective view of a shield according to the present invention.

DETAILED DESCRIPTION OF THE INVENTION

Figure 1:
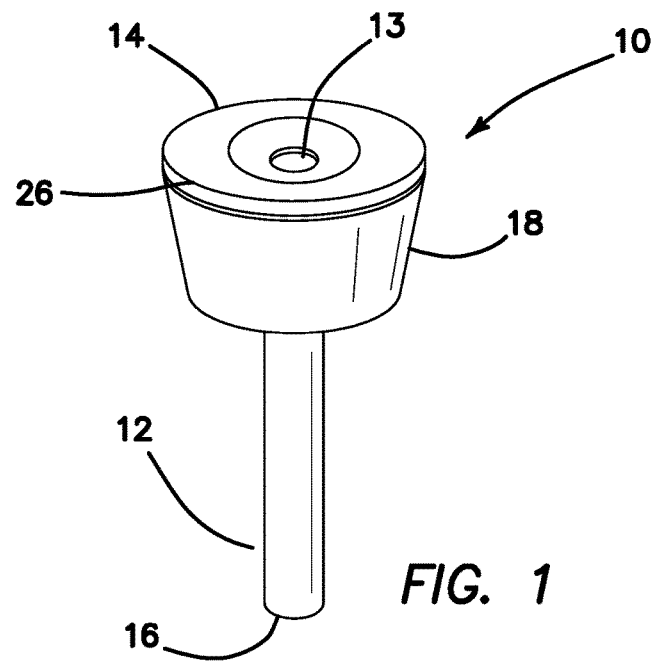
FIG. 1 is a top perspective view of a surgical access device according to the present invention.
Figure 3:
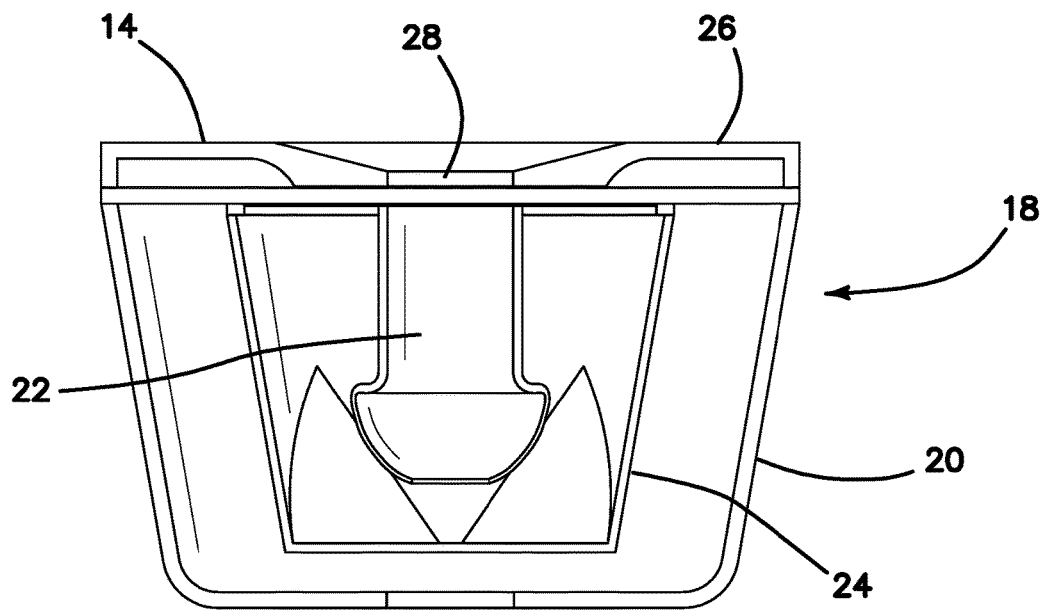
FIG. 3 is a cross-sectional view of a seal assembly and housing according to the present invention.
Figure 2:
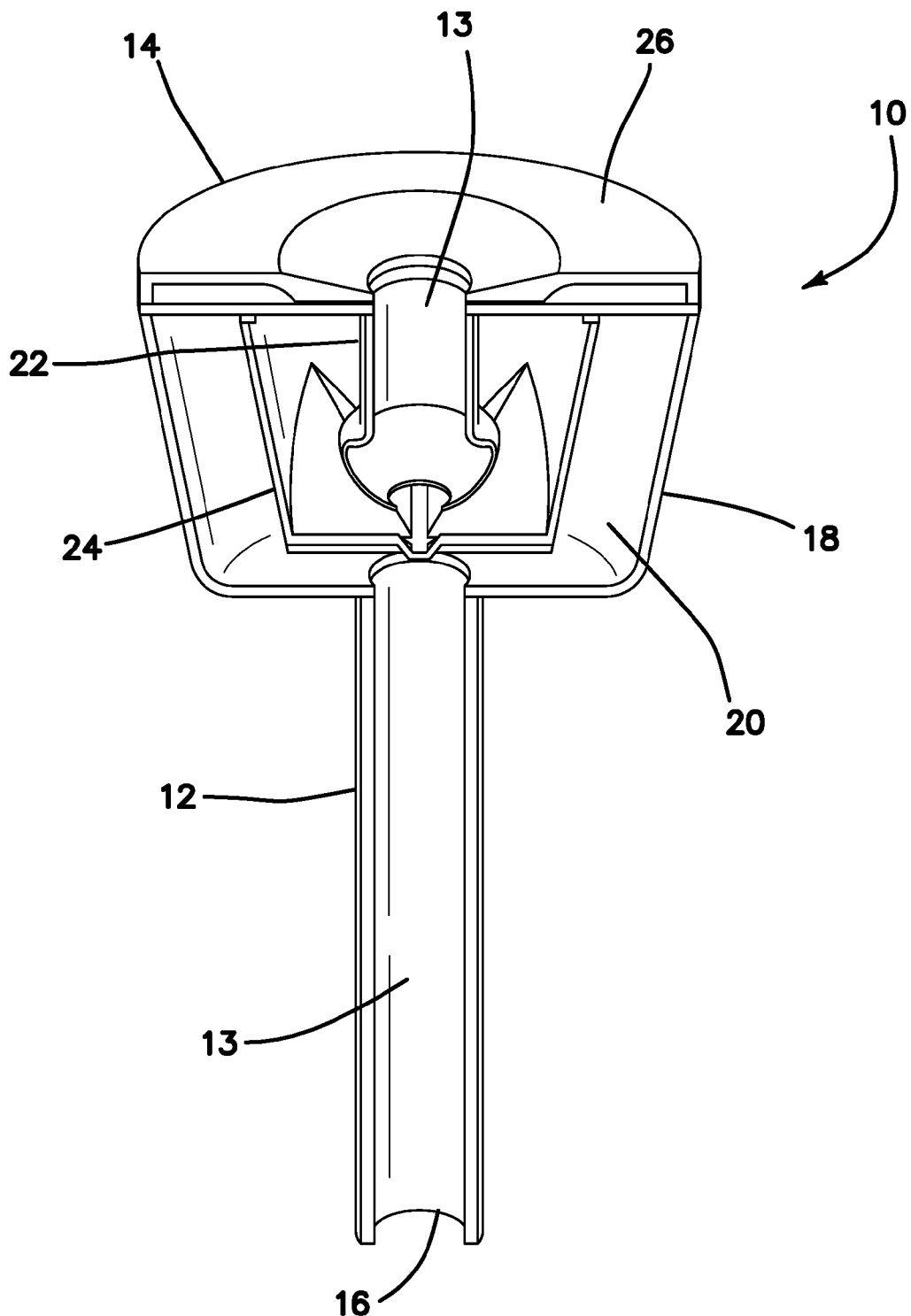
FIG. 2 is a cross-sectional view of a surgical access device according to the present invention.

Turning to FIGS. 1-3, there is shown a surgical access device 10. One type of surgical access device 10 is called a trocar 10. A trocar 10 provides access to the inside of a patient, such as to the abdominal cavity, during a surgical procedure such as during a laparoscopic procedure. Laparoscopy is a minimally invasive procedure typically performed through 2-5 small incisions in a patient's abdomen using a camera for visualization. Trocars 10 are placed within each incision and surgical instruments, along with a camera, are passed through them. The surgical access device comprises an elongate tubular structure commonly referred to as a cannula 12 that extends along a longitudinal axis from a proximal end 14 to a distal end 16. The cannula 12 has a central lumen 13 through which instruments are passed. The central lumen 13, which extends between openings at the proximal end 14 and the distal end 16, is dimensioned to accommodate a range of instruments, for example, instruments of predetermined diameters and lengths such as scissors, dissectors, graspers and scopes.

The cannula 12 is inserted through a tissue or body wall and into a body cavity which is pressurized to create an inflated working space for the surgical procedure. At the proximal end 14, a trocar seal or seal assembly 18 is provided. Located at the top of the cannula 12, the seal 18 allows instruments to pass through the cannula 12 while preventing air from escaping from the abdominal cavity. Maintaining proper air pressure is key during a laparoscopic procedure because it allows surgeons an adequately large working space to properly view the surgical field and perform the procedure. The proximal end 14, where the seal assembly 18 is located, has a larger diameter compared to the lower end of the cannula 12, thereby defining a volume in which components of the seal assembly 18 are disposed as best seen in FIGS. 2 and 3. The enlarged proximal portion defining the seal assembly 18 may be integrally formed with the narrower distal portion of the trocar 10, or alternatively, the seal assembly 18 may be configured for releasably connecting to a distal cannula portion. In either case, the longitudinal axis and central lumen of the seal assembly 18 is generally coincident with the longitudinal axis and central lumen of the cannula 12, and which together, define an access channel 13 through the trocar 10. In some cases, the trocar 10 is provided with an obturator (not shown) that is inserted into the central lumen 13 and dimensioned to extend past the distal end of the trocar 10. The obturator has a tissue penetrating tip that facilitates insertion of the trocar 10 into the patient. When inserted into a patient, the obturator is removed and replaced with instruments for performing the surgical procedure.

The surgical access device 10 is typically manufactured in a range of sizes to accommodate instruments of different diameters, for example, up to about 5 mm, 8 mm, 11 mm, 12 mm, or 15 mm. Embodiments of the surgical access device 10 have working cannula lengths of about 55 mm, 75 mm, 100 mm, or 150 mm. These diameters and lengths are exemplary and a wide variety of sizes may be successfully employed with the present invention. The trocar 10 comprises any suitable material, for example, a biocompatible material. In some embodiments, the cannula 12 comprises a polymer, for example, polycarbonate, polyvinyl chloride (PVC), polysulfone, polyamide, polyetheretherketone (PEEK), polyolefin, polyether block amide (PEBAX®), polyepoxide, polyurethane, polyacrylate, polyether, acrylonitrile-butadiene-styrene (ABS), blends, mixtures, copolymers, and the like. In some embodiments, the cannula 12 comprises metal, glass, ceramic, and/or fiber. In some embodiments, the cannula 12 comprises a composite, for example, comprising reinforcing fibers, a reinforcing structure, a layered structure, and the like.

The seal assembly 18 comprises an instrument seal 22, and a zero seal 24 located inside a housing 20 and a cap 26 at the proximal end 14. The cap 26 engages the proximal end of the housing 20 and has a central opening 28 leading into the central lumen 13. The seal housing 20 comprises a generally hollow cylinder open at both ends and includes a generally circular step, stop or flange 30 located inside the housing that projects circumferentially inwardly from the inner surface of the wall toward the central lumen 13 which contacts one or more of the seals 22, 24. The first and second seals 22, 24 are generally connected to the trocar 10 by being captured between the cap 26 and housing flange 30 as will be described in greater detail below.

The housing 20 may further include a gas inlet port (not shown) comprising a valve. The gas inlet port fluidly connects the interior of the cannula 12 with a source of gas, for example, an insufflation gas, such as carbon dioxide, for delivery into the cannula lumen 13 and into the surgical site. Some embodiments of the surgical access device 10 comprise a housing 20 is separable from the cannula 12.

The seal assembly 18 will now be described in greater detail. The zero seal 24 prevents gas from escaping the pressurized body cavity through the cannula 12 when no surgical instrument is within the working channel 13 or central lumen 13. The zero seal or check valve 24 is shown in the figures as a double-duck-billed seal or valve. The seal 24 has a plurality of cuts and folds configured to create a plurality of flaps that closing a distal opening of the seal 24. When there is no instrument inserted through the zero seal, the flaps are closed and no fluid passes across the seal 24. When an instrument is inserted, the instrument displaces the flaps of the zero seal 24 allowing it to pass across the seal 24. The seal 24 may be any suitable seal such as duck-billed seal or flap seal that completely halts passage of gas across the seal 24. The instrument seal 22 is located inside the zero seal 24.

Figure 4A:
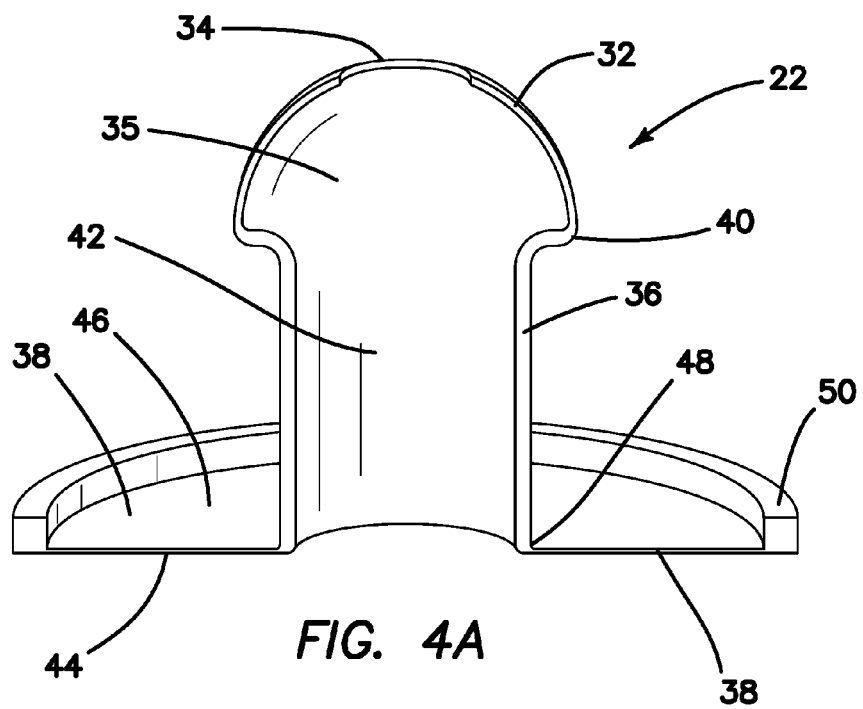
FIG. 4A is a cross-sectional view of an instrument seal according to the present invention.
Figure 4B:
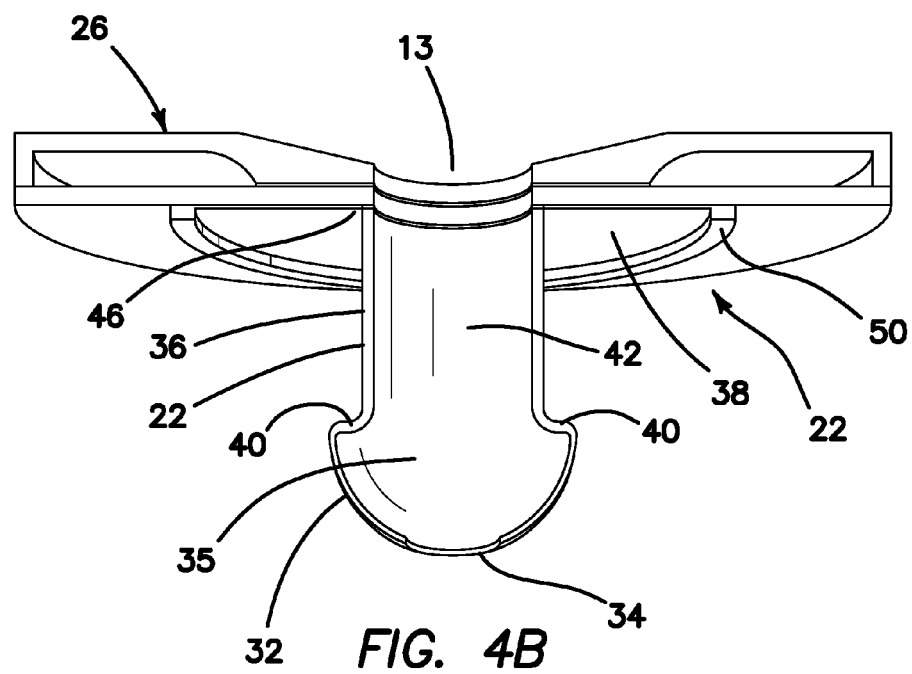
FIG. 4B is a cross-sectional view of an instrument seal and housing cap according to the present invention.

Turning now to FIGS. 4A-4B, a variation of the instrument seal 22 according to the present invention is shown. The instrument seal 22 is configured to seal against an instrument to prevent gas from escaping the pressurized body cavity through the cannula 12 when an instrument is inside the working channel 13. When an instrument is extending across the seal assembly 18, the instrument seal 22 is configured to contact the instrument and to conform around it as much as possible and to remain sealed against it through the many orientations of the instrument with respect to the instrument seal 22. The instrument may be displaced inside the central lumen 13 and so the instrument seal 22 must actively respond to such displacements and be configured to take a position with respect to the inserted instrument and seal against it as best as possible for all of the possible positions of the instrument in order to prevent the escape of gas across the seal 22. The seal 22 includes an instrument sealing portion or element 32 which may also be called an instrument engaging portion or member 32. The proximal end of the instrument engaging portion 32 is connected to a supporting portion or member 36. And, the proximal end of the supporting portion 36 is connected to a base portion 38. The supporting portion 36 is, therefore, located between the instrument engaging portion 32 and the base portion 38 as shown in the figures.

The instrument engaging portion 32 is enlarged relative to the connected supporting portion 36. That is, the instrument engaging portion 32 has a lateral dimension measured perpendicular to the longitudinal axis of the seal 22 that is larger than the same lateral dimension taken of the supporting portion 36. In one variation, this lateral dimension is a diameter; however, the invention is not limited to circular cross-sections of the seal assembly components. The instrument engaging portion 32 may have many operable configurations according to the present invention and include the following descriptions. The instrument engaging portion 32 is bulbous in shape and forms a mushroom-like head connected to the supporting portion 36. The instrument engaging portion 32 is spherical in shape. The instrument engaging portion 32 is hemi-spherical or semi-spherical or spheric or frusto-spherical. The instrument engaging portion 32 is a spheric section taken between two planes, a first plane and a second plane. The instrument engaging portion 32 is a spheric section taken between two planes, a first plane and a second plane that are perpendicular to the longitudinal axis of the seal 22 and parallel to each other. The instrument engaging portion 32 is a spheric section taken between two planes, a first plane and a second plane wherein the first plane is tangential to the sphere. The instrument engaging portion is a spheric section taken between two planes, a first plane and a second plane wherein the second plane passes through the center of the sphere. The instrument engaging portion is a spheric section taken between two planes, a first plane and a second plane and neither the first plane nor the second plane passes through the center of the sphere. The instrument engaging portion is a spheric section taken between two planes, a first plane and a second plane wherein the first plane is tangential to the sphere and the second plane passes through the center of the sphere. The instrument engaging portion is a spheric section taken between two planes, a first plane and a second plane, and further including a third plane located between the first plane and the second plane, the third plane passing through the center of the sphere. The instrument engaging portion is a spheric section taken between two planes, a first plane and a second plane; the spheric section that does not include a third plane that passes through the center of the sphere. The supporting characteristics of a sphere advantageously work to provide optimum transmission of side-to-side forces while, at the same time, reducing the surface area of material at and/or adjacent to the orifice 34 from contacting an inserted instrument. In other variations of the instrument engaging portion 32, the word "spherical" and "spheric" used above in this paragraph is replaced with "ellipsoidal" or "ellipsoid" and hence, the spheric section may be an ellipsoidal section. Furthermore, the shape of the instrument engaging portion 32 can be any shape, for example, it can be polygonal, or geodesic or other shape and/or include one or more flat and/or curved surfaces. The instrument engaging portion 32 is larger than the supporting portion 36 and forms a dome shape with a distal opening which will be described in greater detail below.

The forward-to-rearward, back-and-forth motion of an inserted instrument presents as a drag force or hysteresis where the seal material is alternatively extended and then invaginated or drawn within the seal orifice 34 to a point where it dissociates from a "break-away" characteristic. There is a relationship between the orifice 34 diameter and the overall volume of the hemispherical cavity 35 that maintains a preferred contact angle between the contact edge of the orifice 34 (and/or material adjacent to the orifice) and the surface of the inserted instrument. That relationship can best be characterized as a condition wherein the circumferential edge of the orifice 34 is substantially planar or at nearly a right angle to the axis of an inserted instrument. As such, the overall volume and spherical size of the instrument engaging portion 32 and cavity 35 are adjusted to correspond to the nominal size of the orifice 34 and, hence, of an inserted instrument. For example, for the insertion of larger instruments, a larger orifice 34 would be required and hence a larger hemispherical portion cavity 35 to provide the proper minimal contact.

The instrument engaging portion 32 includes an orifice 34 at the distal end of the instrument engaging portion 32. The orifice 34 serves as an exit for an instrument passed into the seal 22. The orifice 34 is defined by a closed curve on the surface of instrument engaging portion 32. The closed curve may be a circle, ellipse, or pseudo circle. The orifice 34 is sized and configured to correspond to a range of surgical instrument shaft diameters and/or shapes. The instrument engaging portion 32 is formed with a wall thickness that provides appropriate elasticity but that slightly restricts inordinate elongation as an inserted instrument is moved from side to side within the working channel 13 of the surgical access device 10. A semi-spherical geometry is advantageous because an inserted instrument is not forced into intimate contact with an internal surface as it is directed through the orifice 34 of the seal 22. The semi-spherical geometry advantageously prevents the distal-end features of an inserted instrument from damaging the seal 22 as it is inserted through the orifice 34 off-center. A shield, which will be described in greater detail below, may be provided to protect the internals surface of the seal 22. The instrument engaging portion 32 is substantially larger in diameter or distance measured laterally to the longitudinal axis than the diameter or lateral dimension of the supporting portion 36 to which it is connected regardless or their shapes. The instrument engaging portion 32 includes an inner surface and an outer surface and a cavity 35. The instrument engaging portion 32 comprises a resilient structure of sufficient surface area to allow stretching and folding of the seal material.

The edge of the orifice 34 contacts an inserted instrument. As the inserted instrument is pushed distally, the inner surface of the instrument engaging portion 32 may come into contact with the surface of the instrument. When the inserted instrument is moved proximally, the outer surface of the instrument engaging portion 32 may come into contact with the surface of the instrument. In either case, whether the instrument is moved proximally or distally relative to the seal 22, the shape of the instrument engaging portion 32 minimizes the area of the instrument engaging portion 32 that comes into contact with the inserted instrument, thereby, advantageously reducing the friction and drag exerted on the instrument as well as the degree of hysteresis, stiction and oil canning. The instrument engaging portion 32 is configured to provide the least amount of contact with the instrument in a static or dynamic condition while still providing sealing to prevent the escape of gas across the seal.

The supporting portion 36 is an elongate tubular structure. The supporting portion 36 is cylindrical having an inner surface and an outer surface. The inner surface defines a lumen 42 having a diameter. A wall thickness is defined between the inner surface and the outer surface. The supporting portion 36, at its distal end, is connected to the instrument engaging portion 32 forming an intersection 40. The intersection 40, which also can be called a flange, undercut, or lip, extends generally radially outwardly from the supporting portion 36. The supporting portion 36, at its proximal end, is connected to the base portion 38. Together, the supporting portion 36 and the instrument engaging portion 32 form a mushroom-like shape wherein the instrument engaging portion 32 defines a head and the supporting portion 36 defines a stem. In one variation, the supporting portion 36 has a wall thickness that is greater than the wall thickness of the instrument engaging portion 32 making it relatively more rigid and less flexible. In another variation, the supporting portion 36 has a wall thickness that is the same as the wall thickness of the instrument engaging portion 32. In another variation, the supporting portion 36 is rigid or semi-rigid relative to the instrument engaging portion 32. The supporting portion 36 is configured to have the smallest diameter that allows passage of an inserted instrument without undue restriction upon the instrument. The diameter of the supporting portion 36 is smaller than the diameter of the instrument engaging portion 32 and the intersection between the two portions 32, 36 is defined by a radially expanding portion that may be straight or curved. The orifice 34 of the instrument engaging portion 32 is coaxial with or aligned with the lumen 42 of the supporting portion 36. The supporting portion 36 is connected at its proximal end to the base portion 38.

The base portion 38 extends radially outwardly from supporting portion 36 forming a circumferentially extending planar portion that encompasses and extends around the lumen 42 of the supporting portion 36. The base portion 38 defines the entryway into the lumen 42 of the supporting portion 36 with the lumen 42 being centrally located within the encompassing base portion 38. The base portion 38 includes a proximal surface 44 and a distal surface 46 defining a wall thickness therebetween. The supporting portion 36 connects with the base portion 38 at an intersection 48. The base portion 38 is extremely yielding, pliable and flexible. The base portion 38 may further include an annular feature 50 sized and configured to provide a gas-tight seal between the seal housing 20 and the cap 26. The annular feature 50 extends distally from the distal surface 46 of the base portion 38. The annular feature 50 forms a ring of greater thickness.

The instrument and zero seals 22, 24 comprise a suitable elastomeric material, for example, rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (Neoprene®), perfluorelastomer (Kalrez®), thermoplastic elastomer (HYTREL®, PELLETHANE®, KRATON®), as well as blends, mixtures, copolymers, and/or composites thereof and the like. They may be made of the same material or of different materials.

The instrument sealing portion 32, supporting portion 36 and the base portion 38 may be molded from an elastomeric material as a single component with each portion having the same thickness. In an alternative variation, the wall thicknesses of portions 32, 36, 38 are not the same. For example, the instrument engaging portion 32 may have a wall thickness of approximately 0.010 inches, the supporting portion 36 may have a wall thickness of approximately 0.020-0.025 inches, the base portion 38 may have a wall thickness of approximately 0.005 inches and the annular feature 50 on the base portion 38 may have a wall thickness of approximately 0.025-0.050 inches. As can be seen from these various thicknesses, the wall thickness of the base portion 38 is thinner than the instrument engaging portion 32 which is thinner than the supporting portion 36. These wall thickness values suggest the principle of operation of the instrument seal 22 of the present invention. In particular, an instrument is inserted into the working channel 13 and closely directed to the orifice 34 along the length of the supporting portion 36. Therefore, there may be no need to shield the instrument seal 22 against the distal end features of an incoming instrument that may tear, stretch or impinge upon the inside surface of the instrument seal 22. Also, once through the orifice 34, the inserted instrument easily displaces the orifice 34 because of the relationship between the position of the orifice 34 and the small-diameter supporting portion 36 connected to the resilient base portion 38. The instrument engaging portion 32 together with the supporting portion 36 are substantially greater in length than the diameter of the supporting portion 36. This arrangement provides a leveraged advantage that allows an inserted instrument to displace the orifice 34 without elongating the orifice 34. Additionally, the relatively thicker and more rigid support portion 36 compared to the instrument engaging portion 32 prevents the instrument seal 22 from being drawn forward upon insertion of an instrument.

In another variation, the supporting portion 36 of the instrument seal 22 is constructed of rigid plastic such as ABS, polycarbonate, PVC or the like while the instrument engaging portion 32 is made of an elastomer of the like listed above. The supporting member 36 may further be connected to a very resilient base portion 38 constructed of an elastomeric material such as silicone, polyisoprene, polyurethane, Krayton® or the like. The base portion 38 may further include a plurality of bellows or convolutions that enhance material compliance as will be described below.

Figure 5:
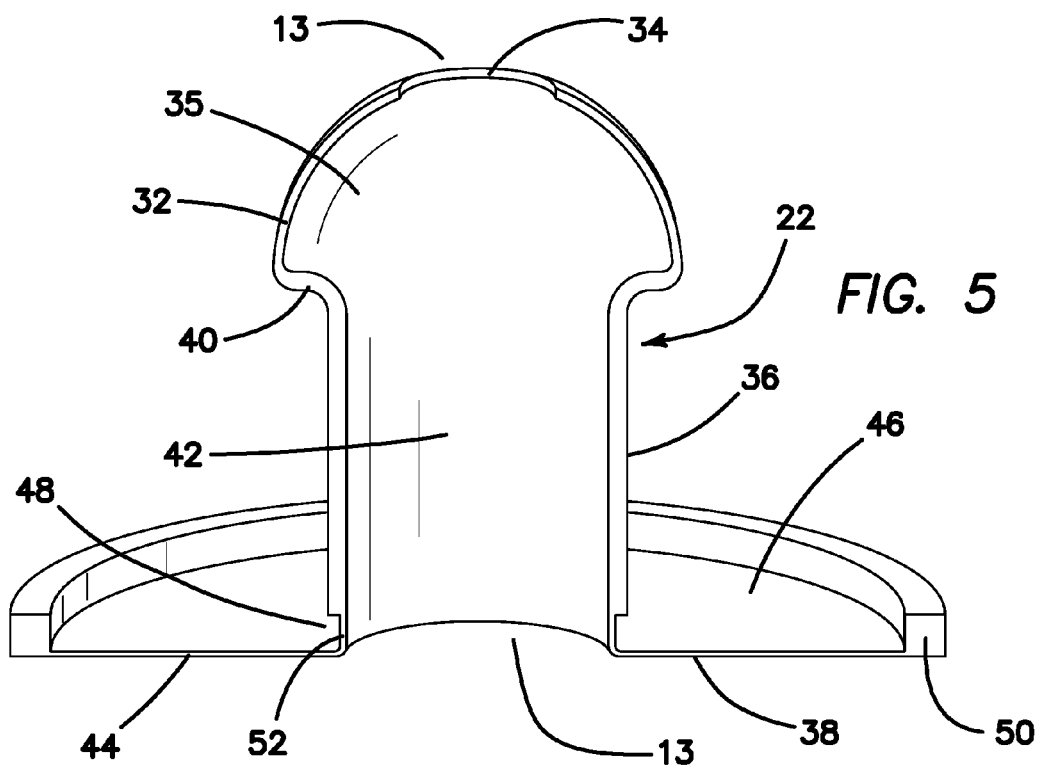
FIG. 5 is a cross-sectional view of an instrument seal according to the present invention.
Figure 6:
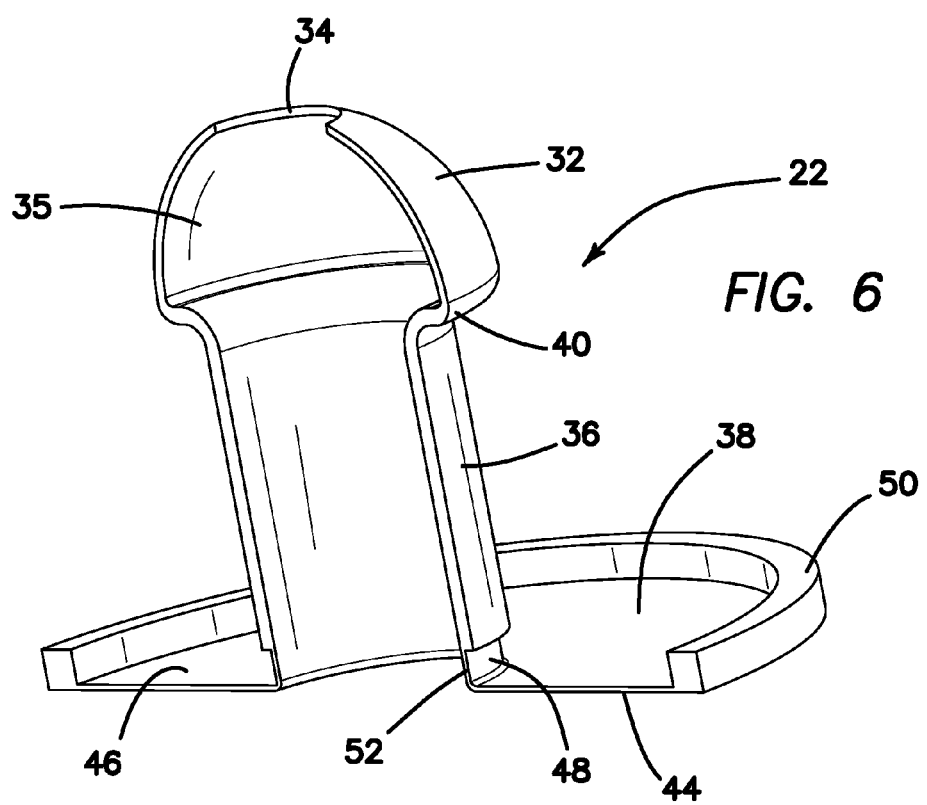
FIG. 6 is a cross-sectional view of an instrument seal according to the present invention.

Turning now to FIGS. 5 and 6, there is shown a variation of the instrument seal 22 according to the present invention. In this variation, the intersection 48 of the supporting portion 36 with the base portion 38 is defined by a wall thickness along the supporting portion 36 that is smaller than the remainder of the supporting portion 38, thereby, forming an undercut or thin-walled extension 52 of reduced wall thickness. In one variation, the undercut or thin-walled extension 52 has the same wall thickness as the base portion 38 as shown in FIGS. 5 and 6. The seal 22 of FIGS. 5 and 6 provides a highly flexible supporting portion 36. The thin-walled extension 52 is sized and configured to allow extreme flexibility from side-to-side, while at the same time, minimizing longitudinal stretch and deformation. The proportion or longitudinal length of the undercut or thin-walled extension 52 is determined by the desired side-to-side flexibility compared to the tolerable amount of longitudinal deformation. The remainder of the supporting portion 36 beyond the thin-walled extension 52 comprises a wall thickness sized and configured to limit elongation, stretch or longitudinal deformation and transmit the forces moving the orifice 34 from side-to-side to the relatively highly flexible portions comprising the thin-walled extension 52 and the adjacent base portion 38 exclusive of the annular feature 50. The relatively thicker distal end of the supporting portion 36 interconnects with the instrument engaging portion 32 at the intersection 40 in which the wall extends outwardly and transitions to the instrument engaging portion 32 having a wall thickness that is thinner than the distal end of the supporting portion 36 which extends distally to the orifice 34 at the distal end of the seal 22. The wall of the instrument engaging portion 32 is sufficiently thick to prevent inappropriate distortion of the orifice 34 or the surrounding material and structure so that it can conformingly and uniformly seal against an inserted instrument. Limiting the elongation of the seal 22 to the highly flexible regions that include the thin-walled extension 52 and the adjacent base portion 38 surrounding and interconnected to the thin-walled extension 52 advantageously provides a seal 22 that is stable and does not present inordinate material drag or friction upon an instrument inserted into the working channel 13. The small linear dimension along the longitudinal axis of the thin-walled extension 52 advantageously limits the amount of linear extension of the seal 22 when an instrument exerts forward or rearward motion when an inserted instrument moves within the working channel 13.

Figure 7:
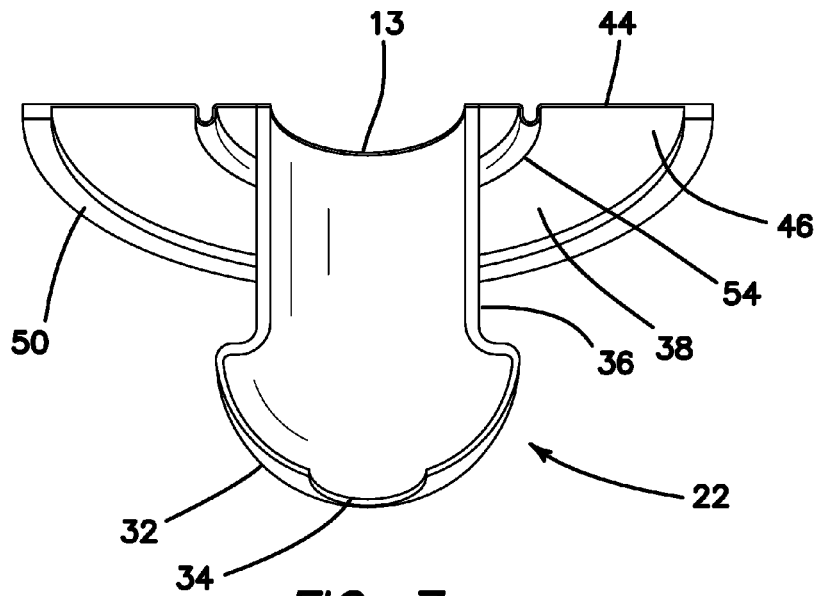
FIG. 7 is a cross-sectional view of an instrument seal according to the present invention.
Figure 8:
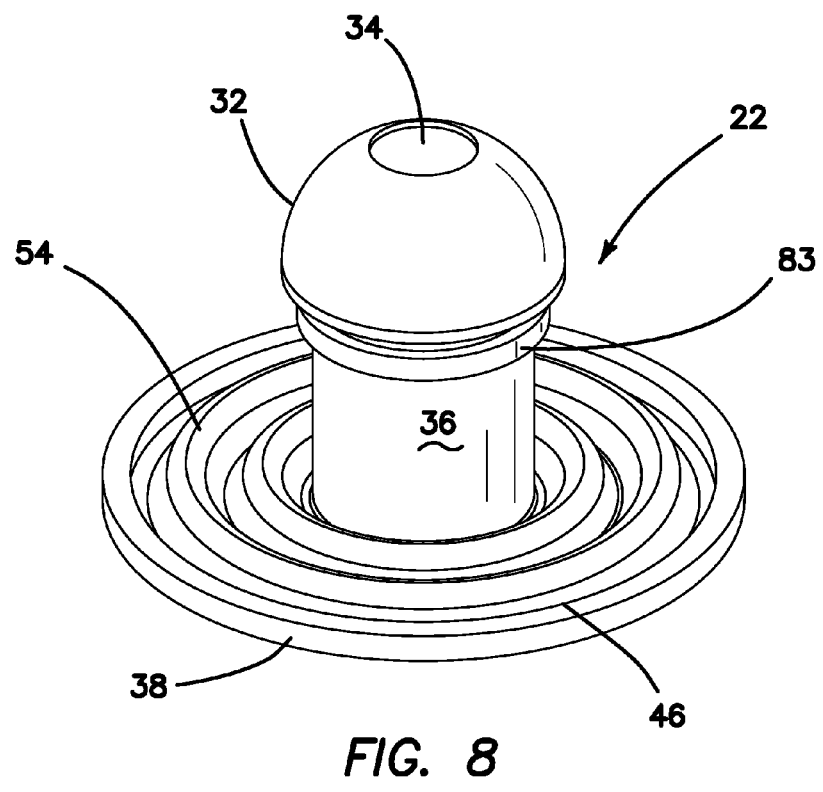
FIG. 8 is a bottom perspective view of an instrument seal according to the present invention.
Figure 9:
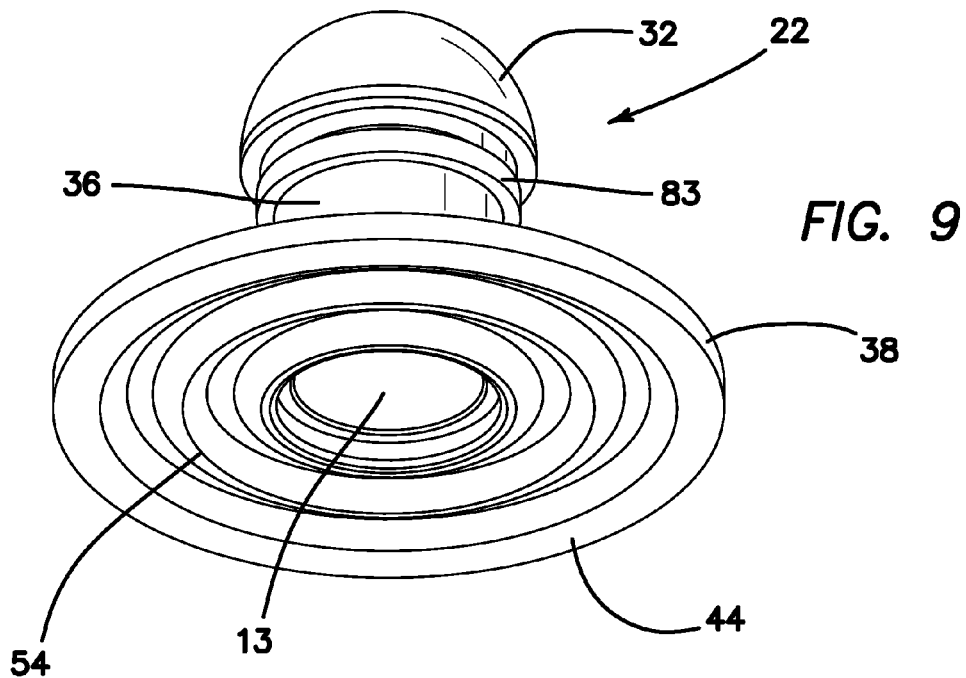
FIG. 9 is a bottom perspective view of an instrument seal according to the present invention.
Figure 10:
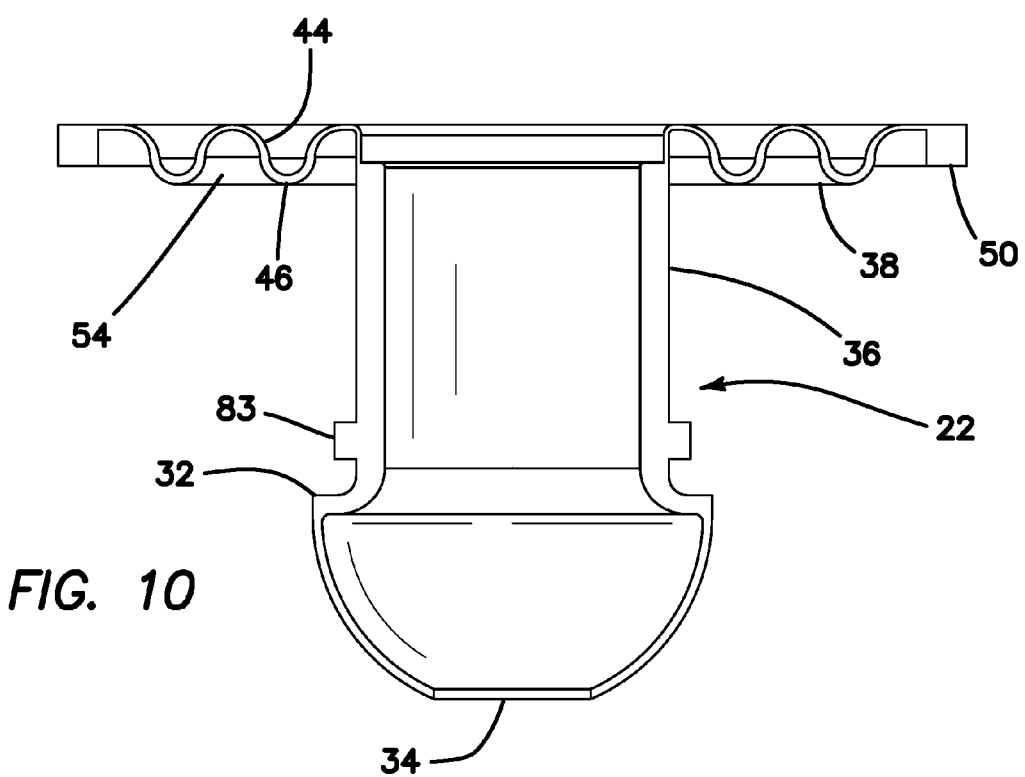
FIG. 10 is a cross-sectional view of an instrument seal according to the present invention.

Turning now to FIGS. 7-10, there is shown a variation of the instrument seal 22 according to the present invention. The base portion 38 includes at least one convolution, fold, crease, bellow, or the like 54. The convolution 54 is formed circumferentially around the working channel 13 or lumen 42 of the supporting portion 36 near the proximal opening of the supporting portion 36. A single convolution 54 is shown in FIG. 7. A plurality of concentric convolutions 54 are illustrated in FIGS. 8-10. The convolutions 54 may have smooth curves or sharp angles at each apex of a combination of both. The convolutions 54 add flexibility and extensibility to the base portion 38. The convolutions 54 advantageously permit the seal 22 to elongate without stretching the elastomeric material which may place undue stress on the material itself or reduce the diameter of the supporting portion 36 if the supporting portion 36 were to elongate along the longitudinal axis. The convolutions 54 are useful in the instance of the seal 22 being sized and configured to accept both large and small diameter instruments. In addition, the convoluted geometry is helpful when the material of the seal 22 is of a high durometer or stiffness.

Figures 11, 12:
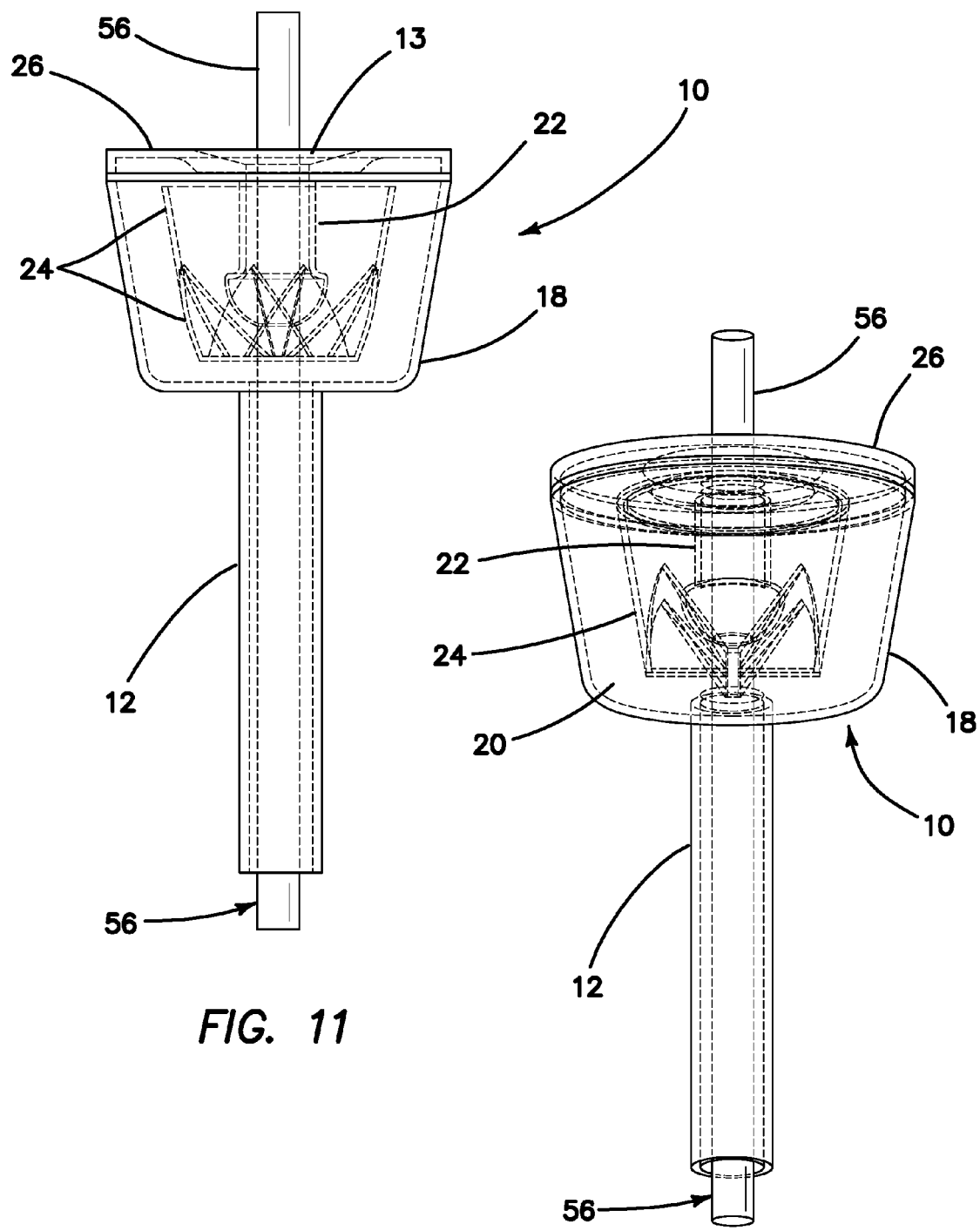
FIG. 11 is a partially transparent view of an instrument inserted into a surgical access system according to the present invention.
FIG. 12 is a partially transparent view of an instrument inserted into a surgical access system according to the present invention.
Figure 13:
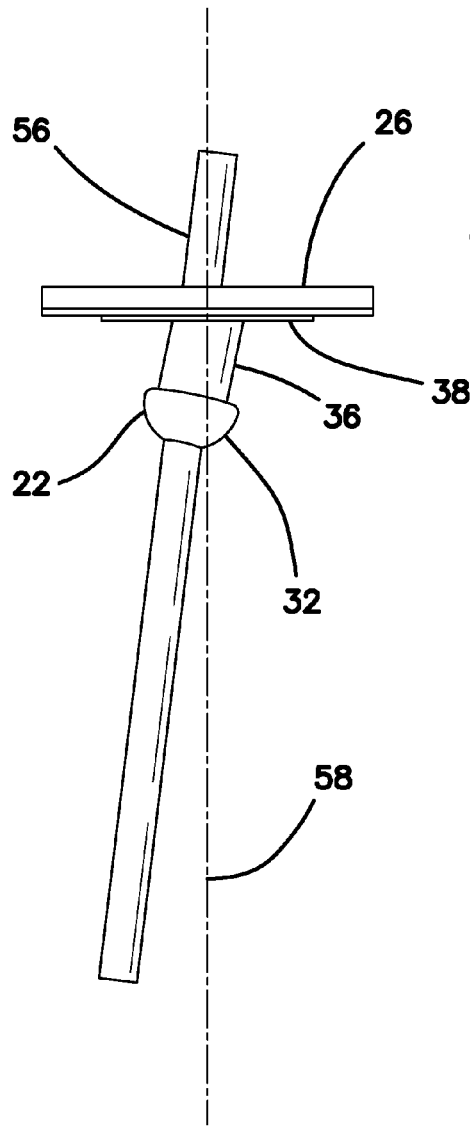
FIG. 13 is a side view of an instrument inserted through a cap and instrument seal according to the present invention.
Figure 14:
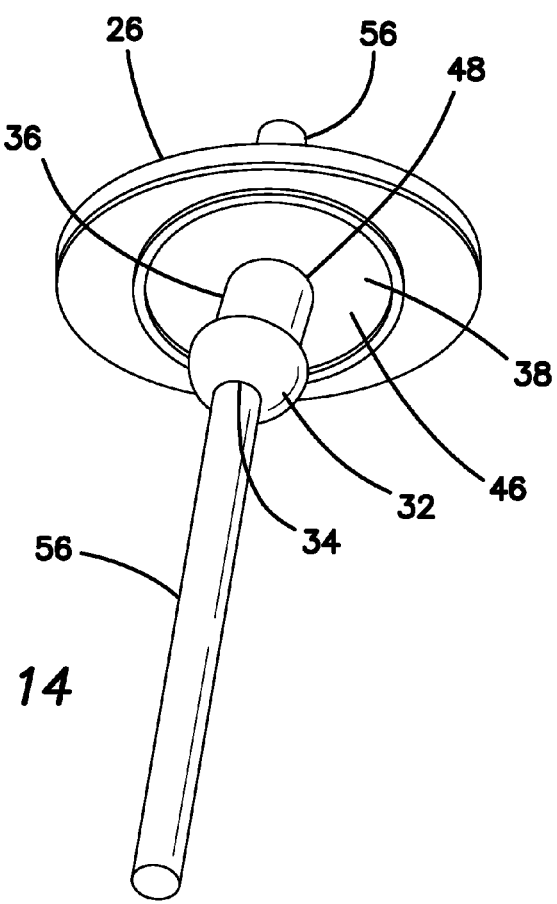
FIG. 14 is a bottom perspective view of an instrument inserted through a cap and an instrument seal according to the present invention.

Turning now to FIGS. 11-14, there is shown an instrument 56 inserted into the trocar 10. In particular, the shaft of an instrument 56 is shown in the figures and the proximal end and the distal end are not shown. In FIGS. 11 and 12, the instrument 56 is inserted into the working channel 13 of the trocar 10 and extends along the longitudinal axis 58 of the trocar 10. FIGS. 11 and 12 illustrate the instrument 56 and the instrument seal 22 in a neutral undeflected configuration. In FIGS. 13-14 the seal housing 20, cannula 12 and zero seal 24 are not shown to illustrate the angulation of the instrument 56 and instrument seal 22 with respect to the longitudinal axis 58 in a deflected configuration. In the deflected configuration of FIGS. 13-14, the supporting portion 36 and the instrument 56 are angled with respect to the longitudinal axis 58. A substantial portion of the base portion 38 is not angled and remains substantially perpendicular to the longitudinal axis 59. Because the seal 22 is connected to the housing 20 and retained by a cap 26, at least a portion of the base portion 38 remains unmoved and the cap opening 28 remains aligned with the lumen 42 of the supporting portion 36 at the proximal end of the seal 22. The side-to-side motion of an inserted instrument and, hence, the side-to-side displacement of the seal 22 at the proximal end near the cap opening 28 is additionally limited by the proximal opening to the lumen 42 of the supporting portion 36 being in alignment with the cap opening 26. Because the cap 26 is rigid, side-to-side displacement of the seal 22 at the cap 26 is constrained by the dimensions of the cap opening 28. Furthermore, side-to-side displacement of the instrument 56 is also limited by the cannula 12 at the distal end of the trocar. The rigid cannula 12 will limit the side-to-side motion of the instrument 56 which in turn limits the side-to-side motion of the seal 22 at the distal end. Because these dimensions are known for a predetermined sized trocar 10, the degree or range of pendulation of the seal 22 is predictable. The present invention in combination with the alignment allows the use of materials that have here-to-for been less than desirable because of the coefficients of friction associated with some of them. For example, a soft silicone elastomer may be used in the present invention since the amount of material in actual contact with the surface of the inserted instrument is minimized relative to traditional seals as will be described further below. Other materials that have not been optimal for existing designs may, therefore, be used including polyurethane, nylon and polyethylene.

Figure 15:
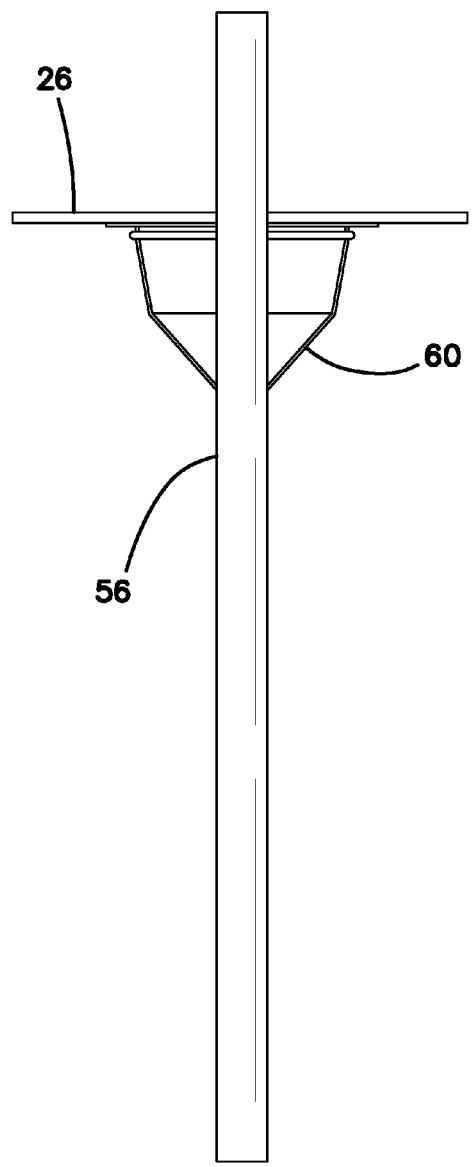
FIG. 15 is a side sectional view of an instrument inserted into a cap and a traditional instrument seal.
Figure 16:
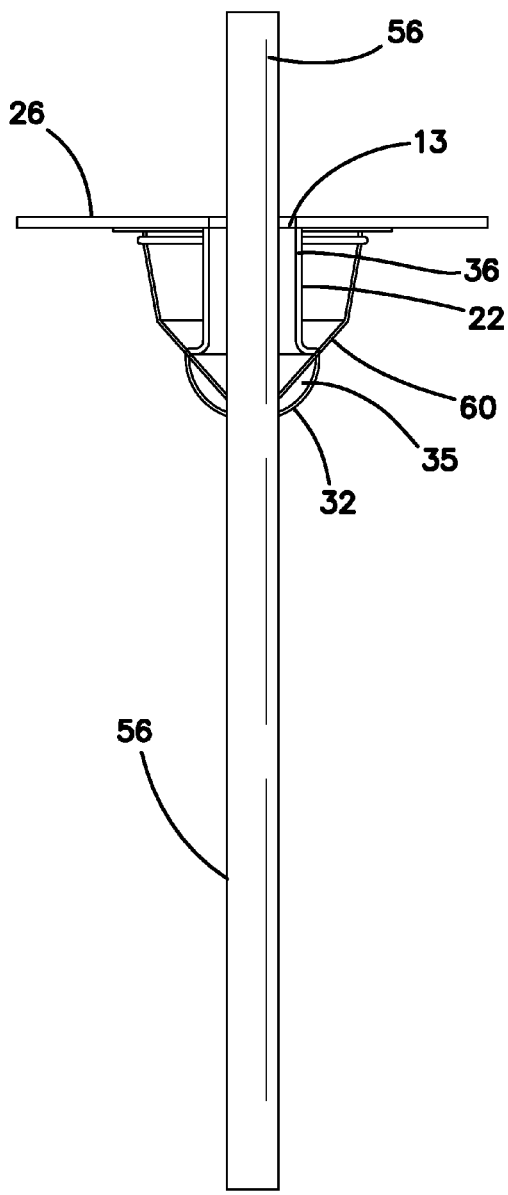
FIG. 16 is a side sectional view of an instrument inserted into a cap illustrating a traditional instrument seal superimposed with an instrument seal according to the present invention.
Figure 17:
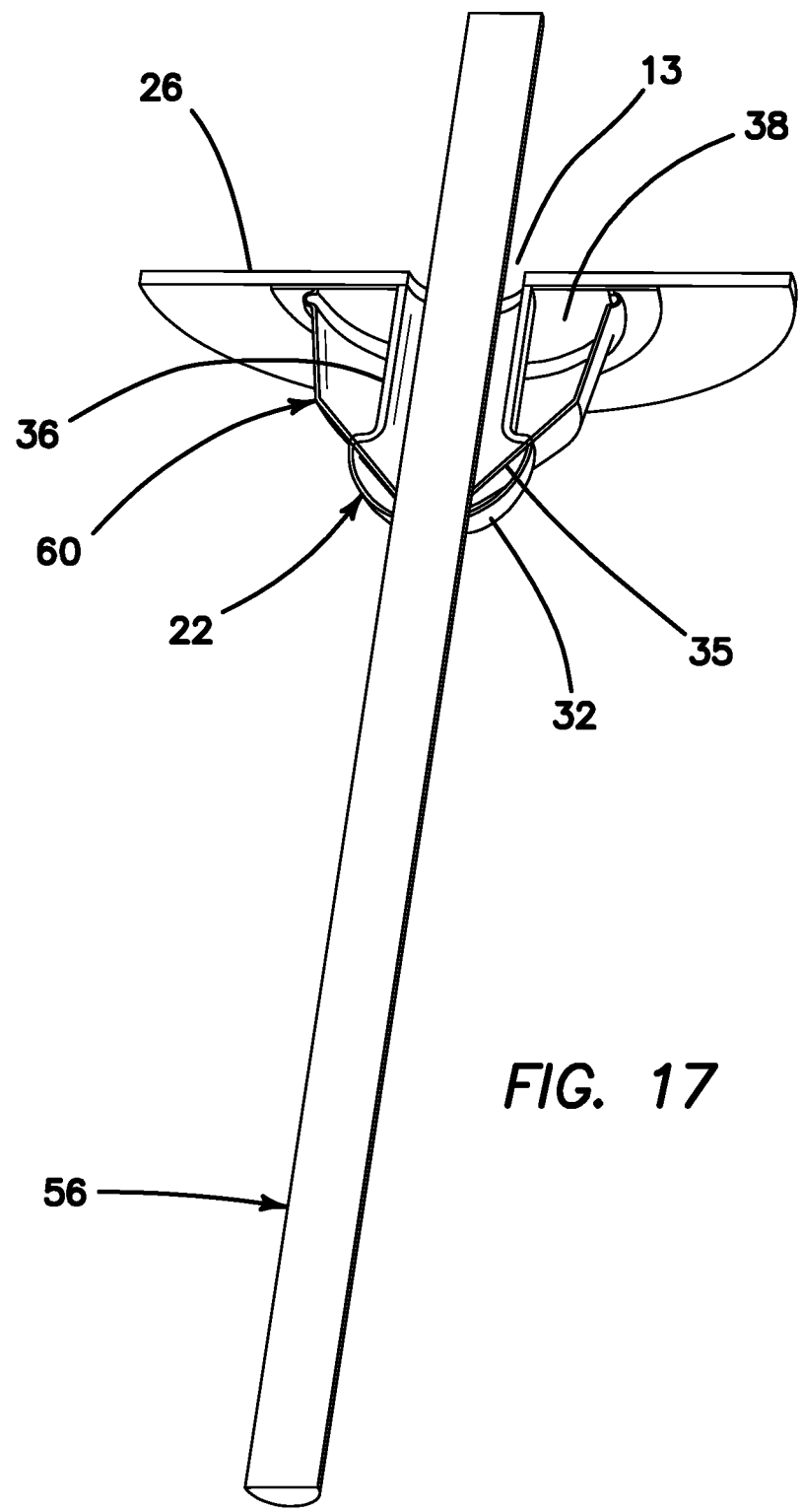
FIG. 17 is a bottom perspective, cross-sectional view of an instrument inserted into a cap with a traditional seal superimposed on an instrument seal according to the present invention.

Turning now to FIG. 15, there is shown an instrument 56 inserted into a cap 26 and through a traditionally-shaped instrument seal 60. The cavity formed by the instrument seal 60 is substantially large relative to the cavity 35 and lumen 42 of an instrument seal 22 according to the present invention as comparatively shown in FIGS. 16-17. In FIGS. 16-17, the traditionally-shaped instrument seal 60 is shown overlaid with an instrument seal 22 according to the present invention. Only the cap 26 and instrument 56 are additionally depicted to illustrate the comparison of seals 22, 60. While the footprint at the cap 26 is substantially the same for both seals 22, 60, the cavity of the traditionally-shaped instrument seal 60 is quite large compared to the instrument seal 22 of the present invention even though the longitudinal length of both seals 22, 60 are nearly the same with the instrument seal 22 of the present invention being slightly longer. In the present invention, the cavity 35 is located distally at the end of the supporting portion 36 of the seal 22. The cavity 35 of the present invention is at a location where the traditionally-shaped instrument seal 22 is tapering in a substantially conical fashion to a reduced-sized distal end. In contrast, the cavity 35 of the instrument seal 22 of the present invention is relatively enlarged at the distal end when compared to the traditionally-shaped seal 60. Similarly, the supporting portion 36 of the present invention is narrower at the proximal end than the proximal end of the traditionally-shaped seal 60. Furthermore, FIGS. 16-17 clearly illustrate the conforming supporting portion 26 of the instrument seal 22 to the shape and diameter of the inserted instrument 56. The supporting portion 26 has a diameter slightly larger than the diameter of an inserted instrument 56. In comparison, the diameter of the traditionally-shaped seal 60 is much larger along the length of the supporting portion 36. The substantially equivalent footprint near the cap 26 permits the seal 22 of the present invention to be easily substituted for the traditionally-shaped seals 60 without changing the dimensions of the housing 20, seal assembly 18 or trocar 10 itself.

Figure 18A:
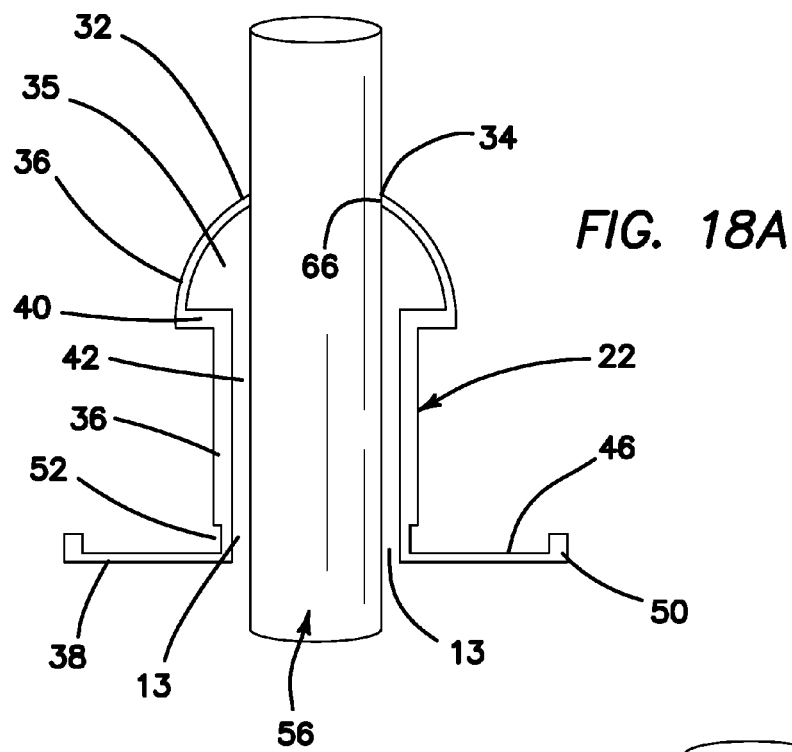
FIG. 18A is a cross-sectional view of an instrument inserted through an instrument seal according to the present invention.
Figure 18B:
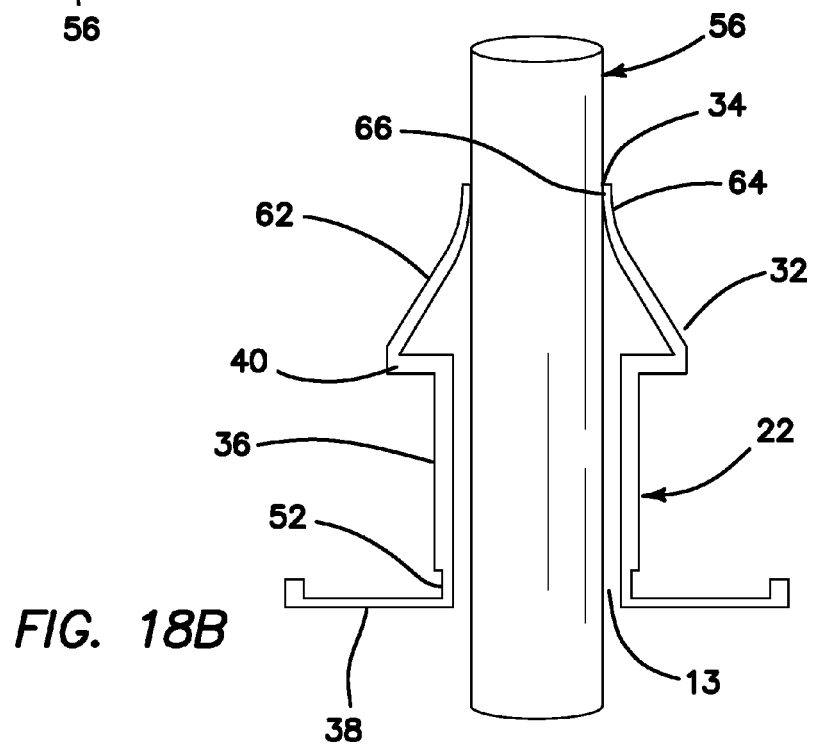
FIG. 18B is a cross-sectional view of an instrument inserted through an instrument seal according to the present invention.

With reference to FIG. 18A, there is shown an instrument seal 22 according to the present invention with an instrument 56 inserted into the working channel 13 of the seal 22 in a normal, static, undeflected configuration. FIG. 18B illustrates another variation of the instrument seal 22 according to the present invention in which the supporting portion 36 and the base portion 38 are substantially identical to the supporting portion 36 and base portion 38 of FIG. 18A. In FIG. 18B, the instrument engaging portion 32 has a different shape. Distal to the intersection 40, the instrument engaging portion 32 of FIG. 18B includes a substantially conical portion 62. In one variation, the outer surface is slightly concave as shown. In another variation, the conical portion 62 transitions distally to a substantially cylindrical portion 64. In another variation, the cylindrical portion 64 is the result of an inserted instrument 56 expanding the orifice 34 such that the inner surface of the instrument engaging portion 32 contacts the outer surface of the instrument 56 which is in contrast to FIG. 18A, in which the inner edge of the orifice 34 contacts the outer surface of the instrument 56. As can be seen in FIGS. 18A and 18B, the contact surface 66 of FIG. 18B is greater than in the variation shown in FIG. 18B.

Figure 19A:
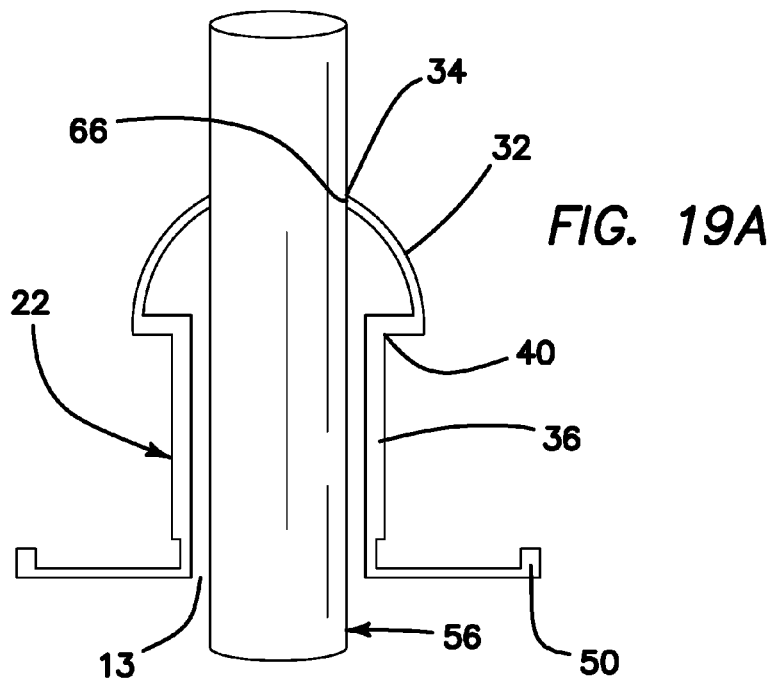
FIG. 19A is a cross-sectional view of an instrument inserted through an instrument seal according to the present invention.
Figure 19B:
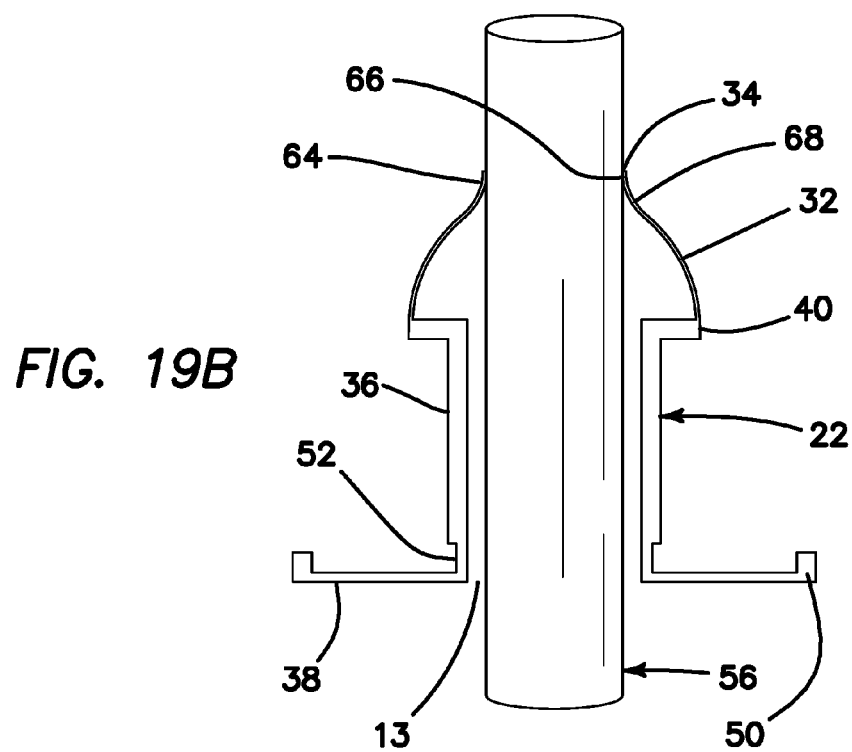
FIG. 19B is a cross-sectional view of an instrument inserted through an instrument seal according to the present invention.

With reference to FIGS. 19A and 19B, there is shown another side-by-side comparison of two instrument seals 22 with an inserted instrument 56 in a normal, static, undeflected configuration wherein like reference numbers are used to describe like parts. FIG. 19A is substantially similar to the embodiments shown and described above in FIGS. 1-18A. FIG. 19B illustrates another variation of the instrument seal 22 according to the present invention in which the supporting portion 36 and the base portion 38 are substantially identical to the supporting portion 36 and base portion 38 of FIG. 19A. In FIG. 19B, the instrument engaging portion 32 has a different shape and a different material thickness compared to FIG. 19A. Distal to the intersection 40, the instrument engaging portion 32 has a reduced wall thickness compared to FIG. 19A. Also, distal to the substantially spherical (or ellipsoidal) instrument engaging portion 32, the instrument engaging portion 32 transitions to a substantially conical or cylindrical portion 64 forming a point of inflection at the point of transition 68 defining a slightly concave outer surface. In another variation, the cylindrical portion 64 is the result of an inserted instrument 56 expanding the orifice such that the inner surface of the instrument engaging portion 32 contacts the outer surface of the instrument 56 which is in contrast to FIG. 19A, in which the inner edge of the orifice 34 contacts the outer surface of the instrument 56. As can be seen in FIGS. 19A and 19B, the contact surface 66 of FIG. 19B is greater than in the variation shown in FIG. 19A which is likely to increase the amount of friction between the instrument 56 and the seal 22.

Figure 20A:
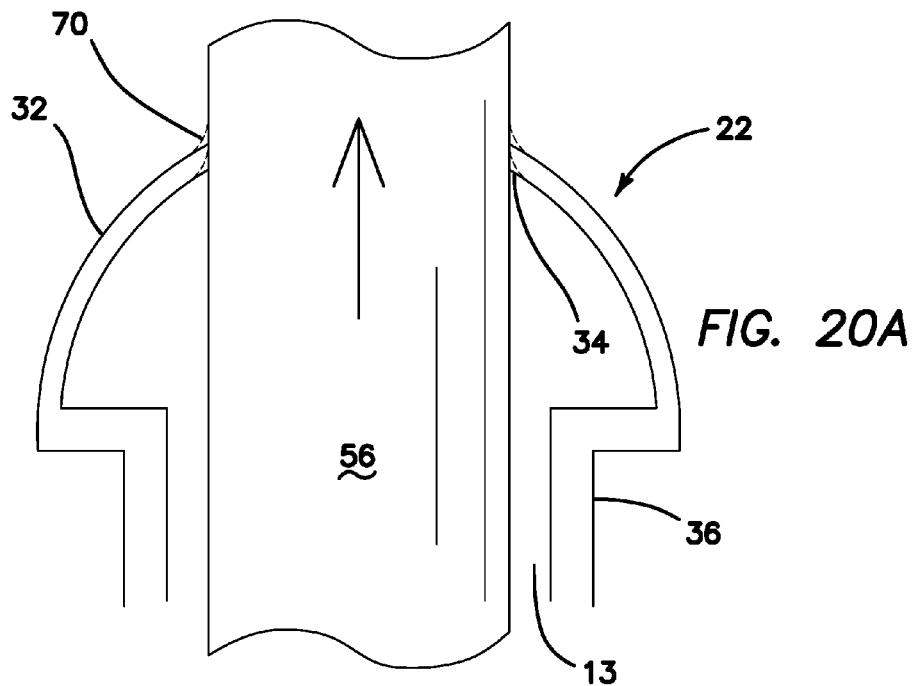
FIG. 20A is a sectional view of an instrument inserted into an instrument seal according to the present invention.
Figure 20B:
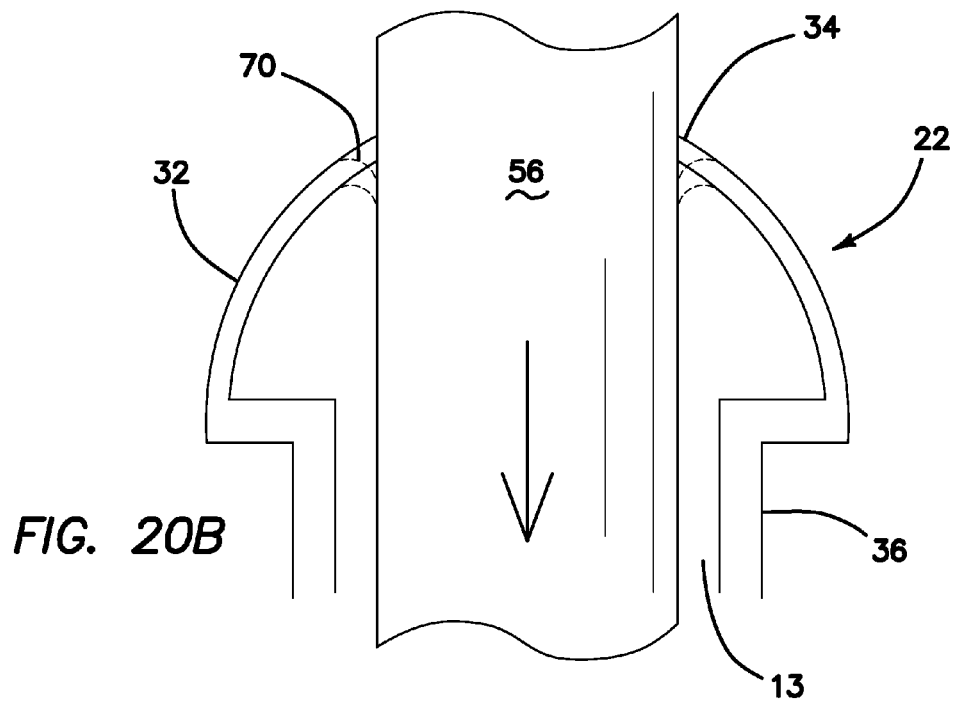
FIG. 20B is a sectional view of an instrument inserted into an instrument seal according to the present invention.
Figure 21:
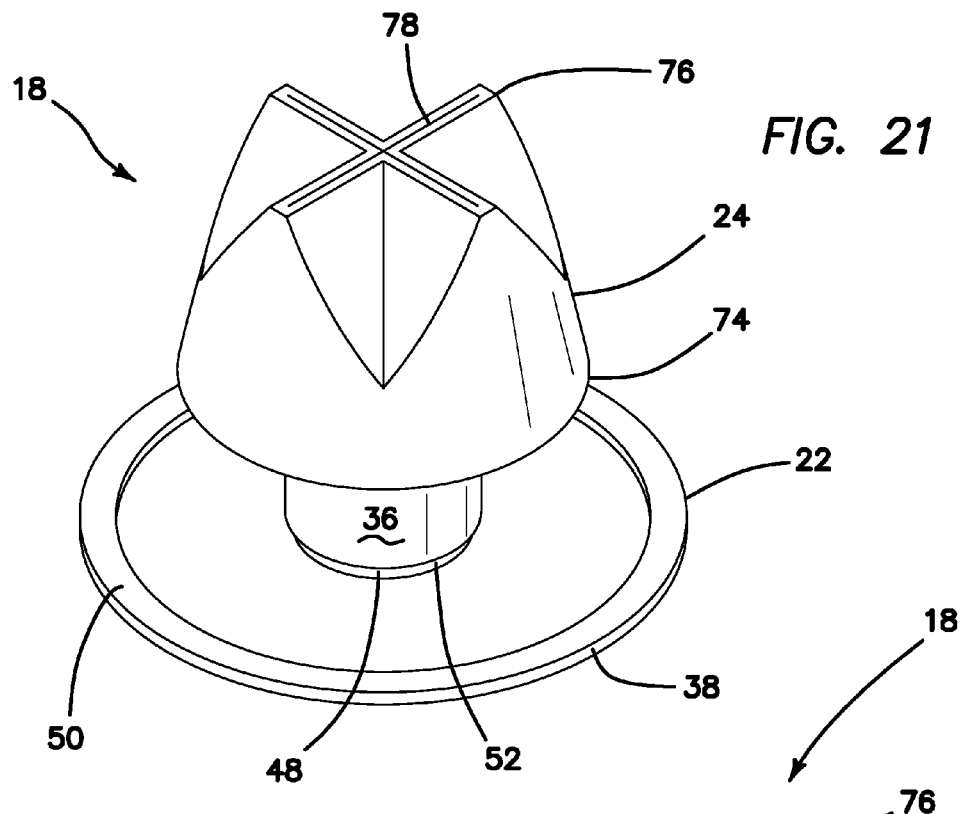
FIG. 21 is a bottom perspective view of an instrument seal and a zero seal according to the present invention.
Figure 22:
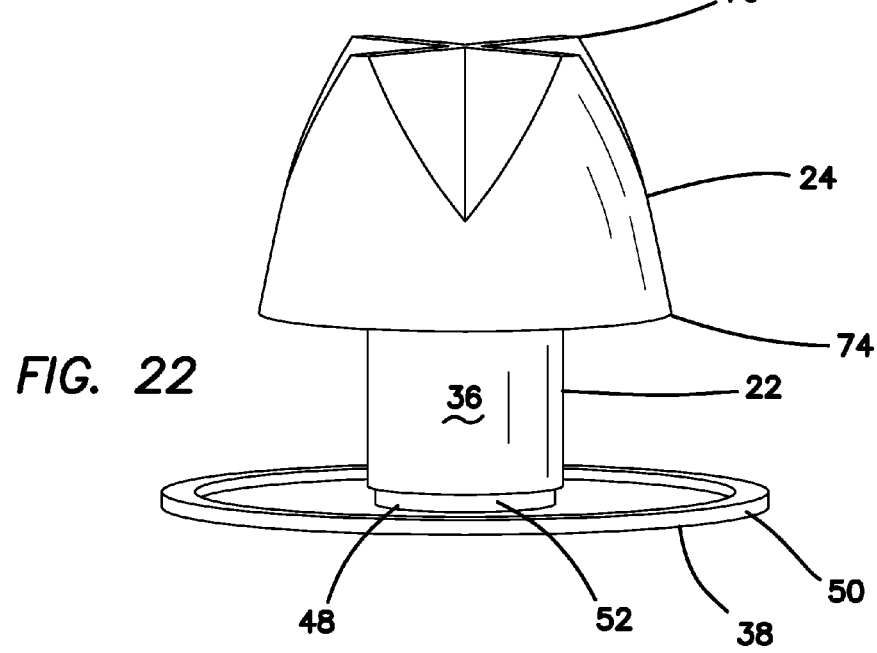
FIG. 22 is a bottom perspective view of an instrument seal and a zero seal according to the present invention.
Figure 23:
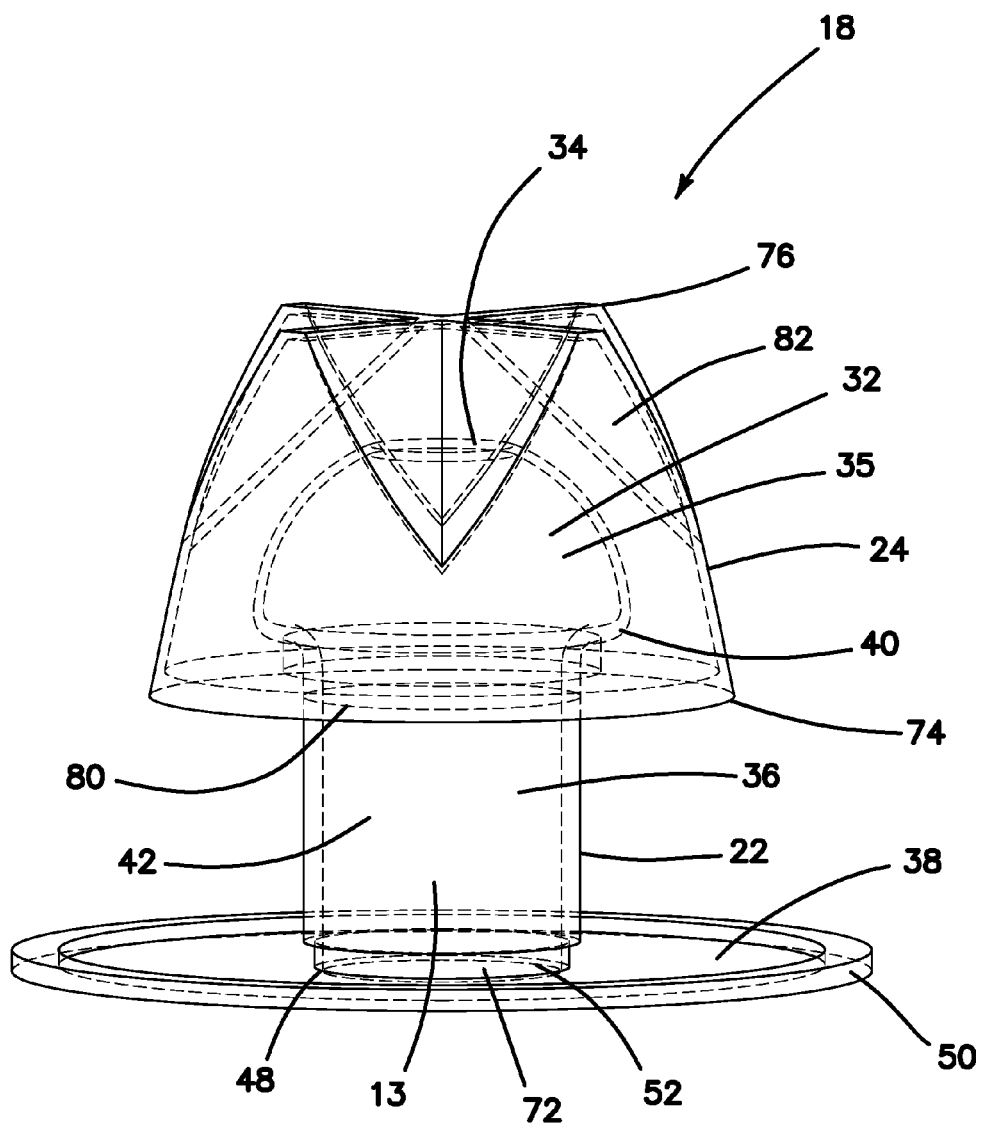
FIG. 23 is a transparent top perspective view of an instrument seal and a zero seal according to the present invention.
Figure 24:
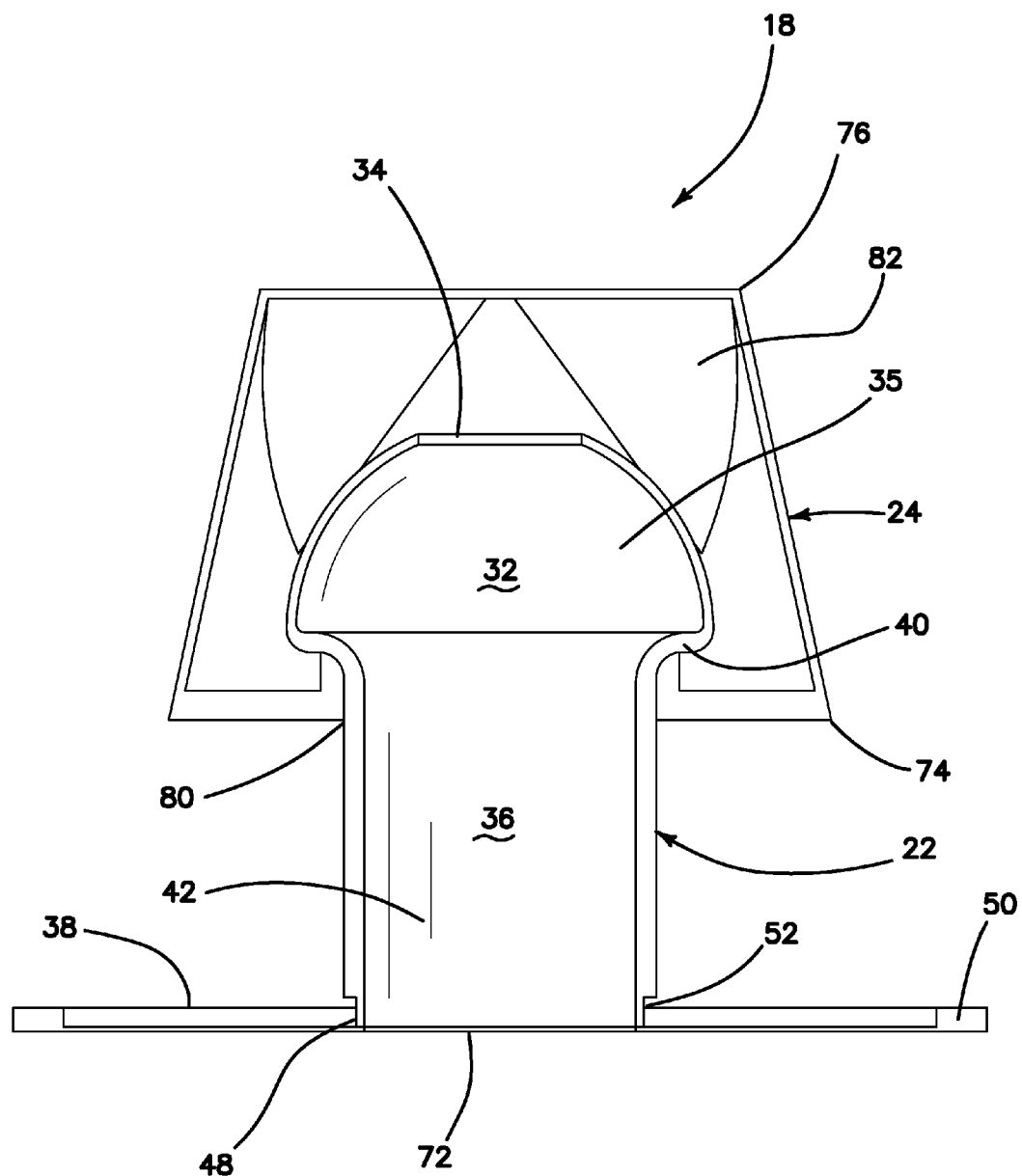
FIG. 24 is a cross-sectional, side view of an instrument seal and a zero seal according to the present invention.

Turning now to FIGS. 20A and 20B, there is shown a distal end of the instrument seal 22 with an instrument 56 inserted into the working channel 13 wherein the dotted lines illustrate dynamic or deflected positions of the instrument engaging portion 32 relative to its static or undeflected positions relative to the inserted instrument 56. In FIG. 20A, the instrument 56 is in a dynamic distal motion forcing the edge of the orifice 34 to be slightly pushed or deflected distally resulting in contact of the orifice edge and possibly a small part of the inner surface of the instrument engaging portion 32 with the distally moving instrument 56 creating a slight concavity or deflection 70 around the orifice 34. FIG. 20B illustrates the instrument 56 moving proximally relative to the seal 22 deflecting or invaginating the instrument engaging portion 32 at a location near the orifice 34. The inward deflection 70 is depicted in dotted lines to contrast the deflected or dynamic position relative to the static or undeflected position of the instrument engaging portion 32 relative to the seal 22. In the deflected position of FIG. 20B, the edge of the orifice 34 and possibly together with a small portion of the outer surface of the seal 22 is in contact with the translating instrument 56.

The geometry of the enlarged instrument engaging portion 32 provides a seal with reduced frictional drag, hysteresis and stiction when an inserted instrument is engaged with the orifice 34. The generally hemispherical geometry in combination with the unusual wall thickness of the instrument engaging portion 32 provides a direct incentive for the undercut 52 to respond to side-to-side motion of an instrument 56 inserted through the distal orifice 34. In addition, it can be seen that the small diameter supporting portion 36 in combination with the overall length of the seal 22 provides a significant leveraged advantage in directing the seal orifice 34 to respond to the side-to-side motion of an inserted instrument 56.

Turning now to FIGS. 21-24, there is shown another variation of the seal assembly 18 comprising an instrument seal 22 connected to a zero seal 24. The instrument seal 22 is substantially identical to the one described above and includes an instrument engaging portion 32, a supporting portion 36 and base portion 38. The supporting portion 36 is interconnected between the instrument engaging portion 32 and the base portion 38. An intersection or undercut 40 is defined between the enlarged bulbous instrument engaging portion 36 and the supporting portion 36 which has a smaller diameter or smaller lateral dimension relative to the instrument engaging portion 32. A working channel 13 extends from an opening 72 at the proximal end of the seal 22 into the lumen 42 of the supporting portion 36 and into the cavity 35 of the instrument engaging portion 32 to an orifice 34 at the distal end of the instrument seal 22. The proximal end of the supporting portion 36 is connected to the base portion 38 at an intersection 48 which may be provided with an undercut or thin-walled extension 52 having a reduced wall thickness relative to the distal end of the supporting portion 36. In one variation, the thin-walled extension 52 is the same thickness as the base portion 38 which includes a relatively thicker annular feature 50 for connection to the housing 20 and cap 26. In particular, the annular feature 50 is captured between the cap 26 and housing 20 permitting the annular base portion 38 inside the circumference of the annular feature 50 to move such as deflect laterally, translated distally, and/or stretch in any direction. The instrument seal 22 is configured to angulate polyaxially and translate along its longitudinal axis. The resiliency of the material of the seal permits some stretch rotation about the longitudinal axis.

The zero seal 24 extends between a proximal end 74 and a distal end 76. The zero seal 24 is shown in FIGS. 21-24 as a double-duckbilled seal; however, the zero seal 24 may be of any configuration that does not permit gas to cross the zero seal 24 when no instrument is inserted. The distal end 76 includes an opening 78 that is shown in a closed configuration in FIGS. 21-24 and opens by force of an inserted instrument. The zero seal 24 includes an opening 80 at the proximal end 74. The inner surface of the zero seal 24 defines a cavity 82. The proximal end 74 of the zero seal 24 is connected to the instrument seal 22 such that the instrument engaging portion 32 of the instrument seal 22 is located inside the cavity 82 of the zero seal 24. The instrument engaging portion 32 snaps through the opening 80 at the proximal end 74 and a circumferential portion of the zero seal 24 seals against the instrument seal 22. The circumferential portion of the zero seal 24 lands proximally of the intersection 40 of the instrument engaging portion 32 and supporting portion 36. The undercut formed by the intersection 40 helps keep the zero seal 24 attached to the instrument seal 22. The instrument seal 22 may further be provided with a circumferential extension or ridge 83 as shown in FIGS. 8-10, 30-33, and 40-42. The ridge 83 extends outwardly from the supporting portion 36. The zero seal 24 is secured to the instrument seal 22 by snapping between the radially extending instrument engaging portion 32 and the circumferential extension 83. In another variation, the instrument seal 22 is integrally formed with the zero seal 24. With the zero seal 24 connected to the instrument seal 22, the distal opening 78 of the zero seal 24 is aligned with the orifice 34 and the lumen 42. In the variation of FIGS. 21-24, the seal assembly 18 is configured such that the zero seal 24 is connected directly to the instrument seal 22. This configuration is different from the variation shown in FIGS. 2-3, 12 wherein the proximal ends of both the zero seal 24 and the instrument seal 24 are connected to the housing 20 by being captured between the cap 26 and the housing 20. With the zero seal 24 connected directly to the instrument seal 22, the zero seal 24 advantageously translates and deflects together with instrument seal 22 as shown in FIGS. 25-33. With the zero seal 24 connected directly to the instrument seal 22, the zero seal 24 conforms closely and responds quickly when the instrument is placed or removed as the zero seal 24 has less distance to assume its closed and sealed configuration. The substantially hemispherical shape of the instrument engaging portion 32 also prevents material drag as the instrument 56 passes through the seal 22. The thicker wall of the supporting portion 36 closely approximates the shape of an inserted instrument such as the cylindrical shape of a shaft of a conventional surgical instrument. The supporting portion 36 translates motion to the relatively thinner sections such as the undercut 52 and the base portion 38. The proximally located base portion 38 is highly responsive and angulation of the supporting portion 36 simultaneously angulates the zero seal 24 in the same direction.

Figure 32:
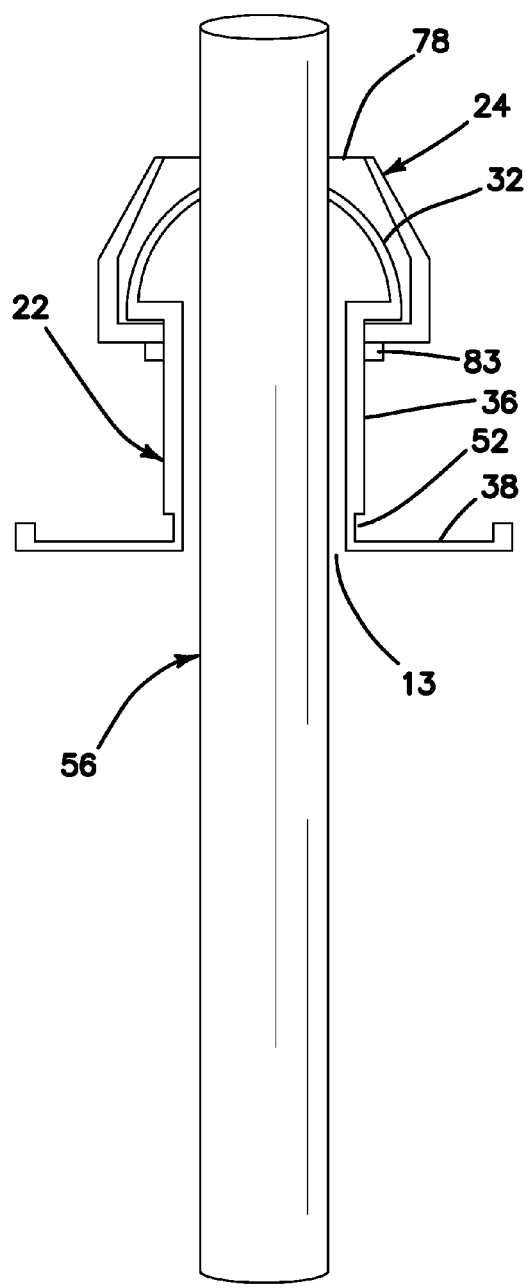
FIG. 32 is a cross-sectional, side view of an instrument inserted through an instrument seal and a zero seal according to the present invention.
Figure 33:
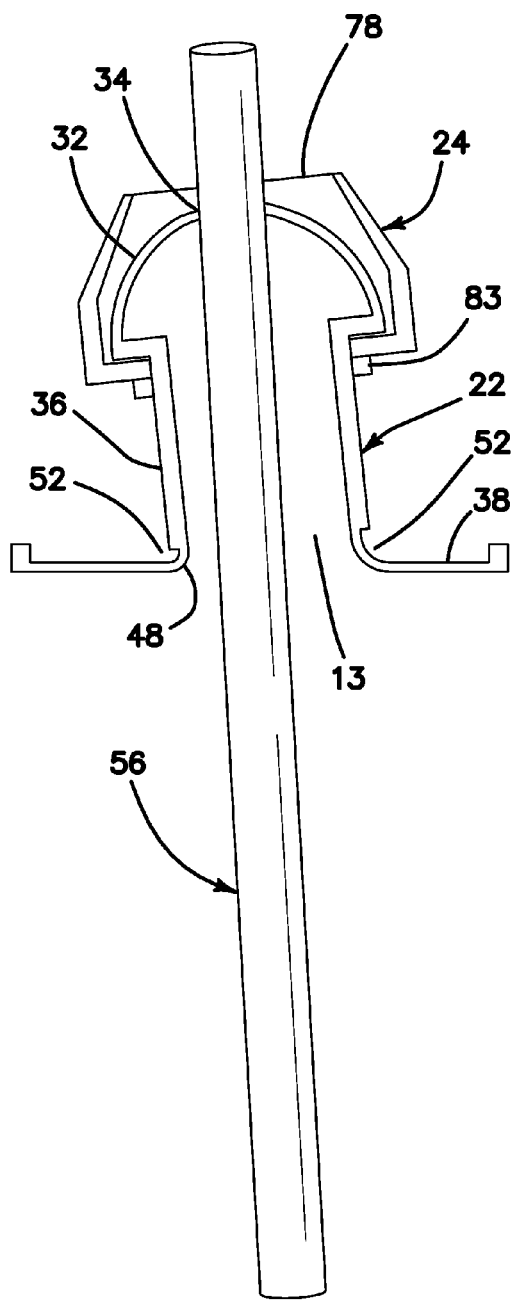
FIG. 33 is a cross-sectional, side view of an instrument inserted through an instrument seal and a zero seal according to the present invention.
Figure 35:
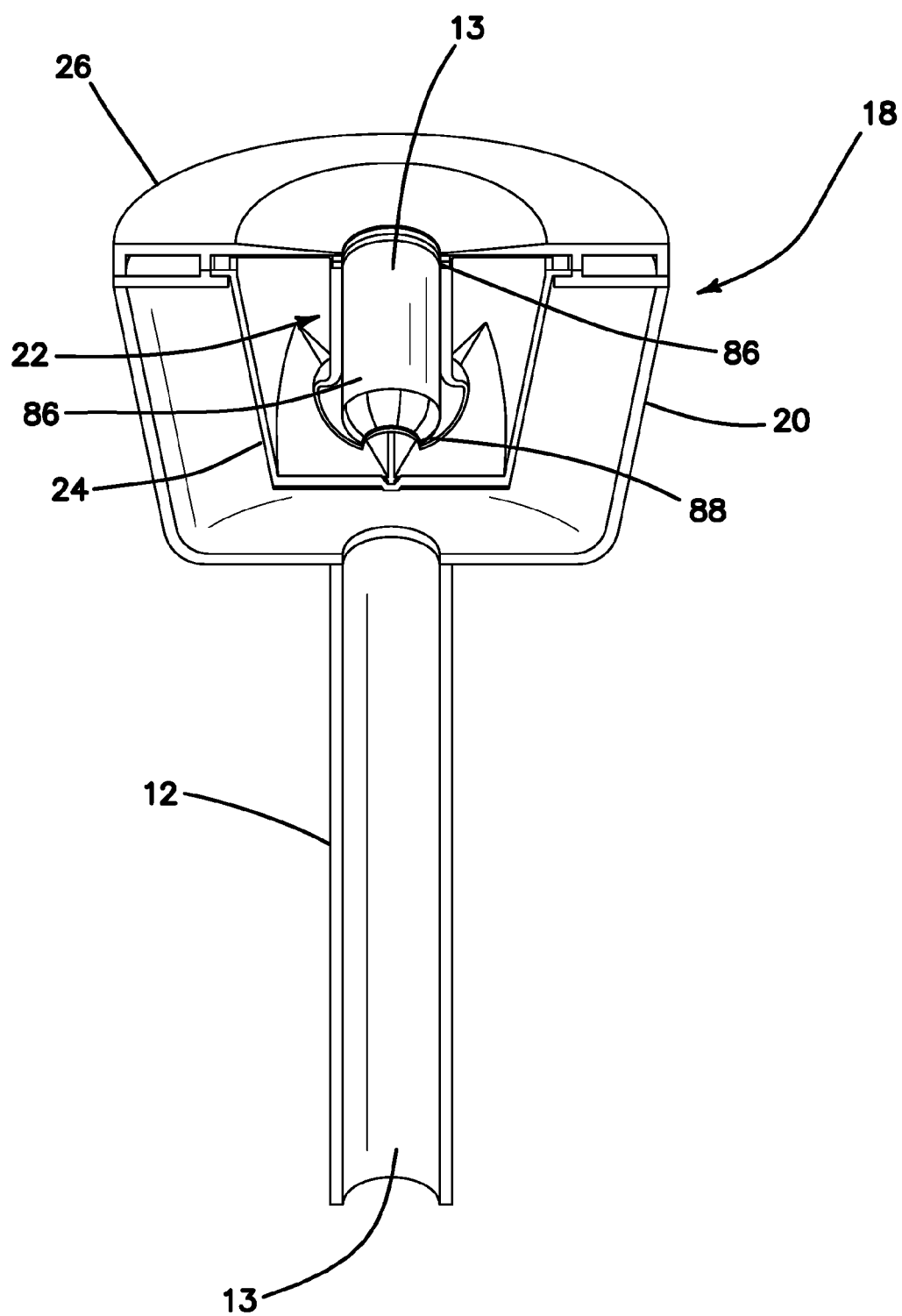
FIG. 35 is a top perspective, cross-sectional view of a shield inserted in a trocar assembly according to the present invention.
Figure 36:
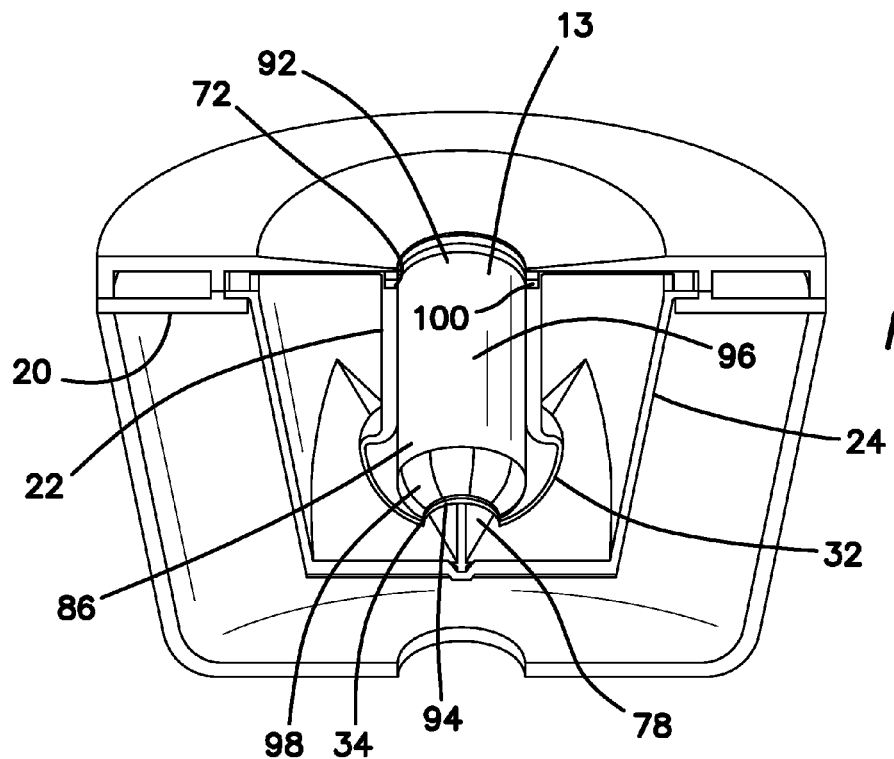
FIG. 36 is a top perspective, cross-sectional view of a shield, a seal assembly and housing according to the present invention.
Figure 37:
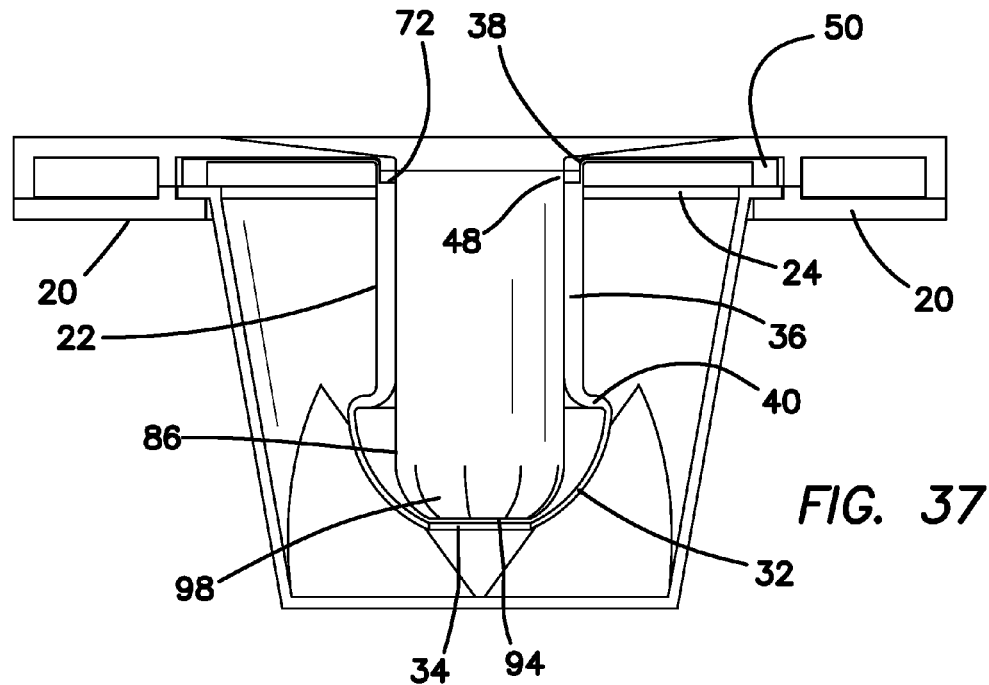
FIG. 37 is a cross-sectional, side view of a shield, a seal assembly and housing according to the present invention.
Figure 38:
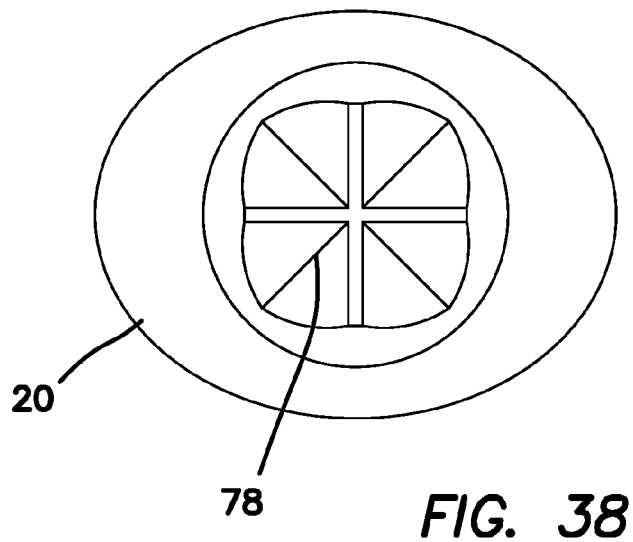
FIG. 38 is a top planar view of a housing and seal assembly according to the present invention.
Figure 39:
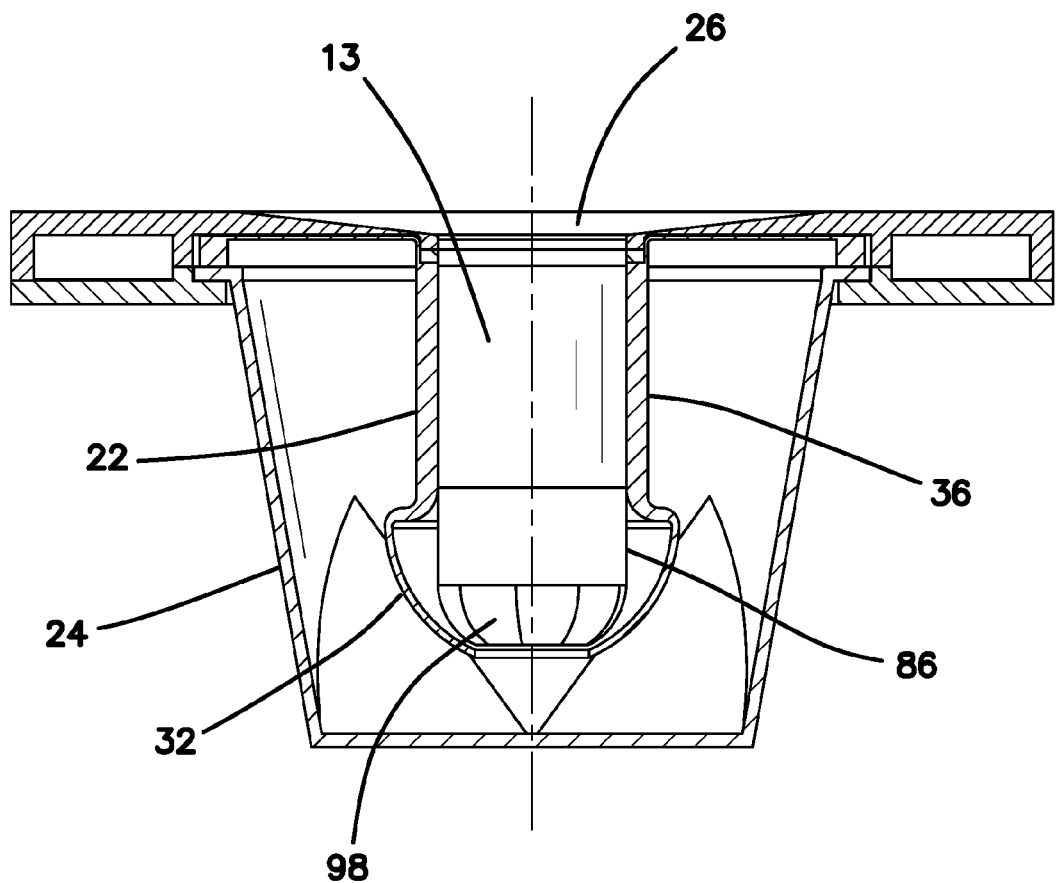
FIG. 39 is a cross-sectional, side view of a shield, a seal assembly and housing according to the present invention.

With particular reference to FIGS. 25-33, the arrangement of the zero valve 24 attached directly to the instrument valve 22 is especially useful when the seal is configured for use with larger diameter instruments 56. It can be seen that a small diameter instrument, deployed within a large diameter working channel 13 will not only engage the orifice 34 but also the opening 78 in the zero valve 24. Instrument 56 contacts with both the zero valve 24 and the instrument valve 22 associated with the distal portion of the combination. This facilitates the transmission of side-to-side movement of a small instrument within a large channel 13 to the highly responsive base portion 38 and undercut 52 and from the instrument seal 22 to the zero seal 24. FIG. 25 illustrates a minimum engagement 84 of the instrument engaging portion 32 with the smallest instrument 56. The seal and instrument 56 are in a static undeflected condition. The orifice 34 is sized for the smallest expected instrument to be inserted providing a minimum engagement 84 of the instrument engaging portion 32 to the instrument 56. FIG. 26 illustrates the instrument 56 inserted into the working channel 13 and angled to deflect the seals 22, 24. The instrument 56 translates the motion to the base portion 38 angulating the instrument seal 22 at the intersection 48 with the base portion 38. It is noted that in the deflected configuration shown in FIG. 26, the orifice 34 and the opening 78 substantially conform around the instrument 56. Also, because the zero valve 24 is connected to the instrument valve 22, both the orifice 34 and the opening 78 in zero seal 24 are in sealing engagement with the instrument 32 and in alignment with each other. FIG. 27 illustrates the seals 22, 24 angled and conforming to the instrument 56 with the instrument 56 translated laterally and not angled. FIG. 28 illustrates the instrument 56 translated even further laterally relative to FIG. 27 and the seals 22, 24 are angled even when the instrument 56 is not angled. The seals 22, 24 sealingly engage the instrument 56 in FIG. 28. In traditional seals, this position would result in the seals 22, 24 separating away from sealing engagement with the instrument 56. FIG. 29 illustrates the instrument not angled and translated in the lateral direction and the seals 22, 24 are not angled. In this configuration, the orifice 24 lacks engagement 84 on one side of the instrument 56. In other words, the orifice 34 would "cateye" or elongate and leak. This degree of engagement would result if the instrument seal 22 did not have the increased flexibility to deflect with respect to the base portion 38 and assume a conforming configuration as in FIGS. 27-28. In FIG. 30, there is shown a seal assembly 18 without an instrument 56. FIG. 31 illustrates an instrument 56 with a small diameter inserted into the working channel 13 in a static, undeflected orientation relative to the seal assembly 18. FIG. 32 illustrates a large diameter instrument 56 relative to the instrument 56 in FIG. 31 inserted through the seal assembly 18. The seal assembly 18 conforms around the inserted instrument 56 to seal against it and prevent the escape of gas. FIG. 33 illustrates a small diameter instrument 56 inserted into the working channel 13 and angled. The instrument seal 22 and the zero seal 24 conform about the outer surface of the instrument 56 at the location of the orifice 34 and opening 78. FIG. 33 illustrates deflection of the seal assembly 18 in the location of the undercut 52 in the location of the intersection 48 of the supporting portion 36 with the base portion 38 where the seal wall thickness is reduced. FIG. 33 also illustrates deformation or stretching of the base portion 38 on the side opposite to the direction of angulation.

Turning now to FIGS. 34-39, there is shown a shield 86 according to the present invention. The shield 86 is a generally tubular, elongate structure having a proximal end 88 and a distal end 90. The shield 86 includes an opening 92 at the proximal end 88 leading into a lumen 96 that is interconnected with an opening 94 at the distal end 90. The lumen 96 of the shield 86 forms at least part of the working channel 13. The shield 86 extends along the length of the instrument seal 22. In one variation, the shield 86 extends only partly along the longitudinal length of the instrument seal 22. The opening 94 at the distal end 90 of the shield 86 is coincident or aligned with the orifice 34 of the instrument seal 22. Also, the proximal end 88 of the shield 86 and its opening 92 is aligned with the proximal opening 72 of the instrument seal 22. The shield 86 is coaxial with the instrument seal 22 and is in close juxtaposition or in contact with the instrument seal 22 so that movement of an inserted instrument is transmitted to the seal assembly. At least part of the distal end 90 of the shield 86 includes a plurality of slits extending from the distal end 90 toward the proximal end 88 forming a plurality of leaflets 98 around the opening 94. In one variation, the instrument seal 22 is slightly modified to accommodate the shield 86. In particular, the intersection 48 of the supporting portion 36 with the base portion 38 forms an undercut 52 in the instrument seal 22 that is located on the inside instead of on the outside. Hence, the outer surface of the supporting portion 36 appears to be smooth across the thin-walled extension 52 with the reduction in the thickness of the wall being seen from inside the instrument seal 22 as an undercut 52. The proximal end 88 of the shield 86 includes a circumferential flange 100 that is sized and configured for mating into the undercut 52 from inside the working channel 13. The shield 86 may also be considered a director 86 placed within instrument seal 22 to help direct an instrument into the working channel 13. The leaflets 98 help direct the instrument toward the orifice 34 of the instrument seal 22 as well as protect the material from tearing or interference. Also, the leaftlets 98 make the distal end 90 of the shield 86 more flexible to unimpede the angulation of an inserted instrument. In FIGS. 34-39, the instrument seal 22 and the zero seal 24 are connected to the housing 20.

Figure 40:
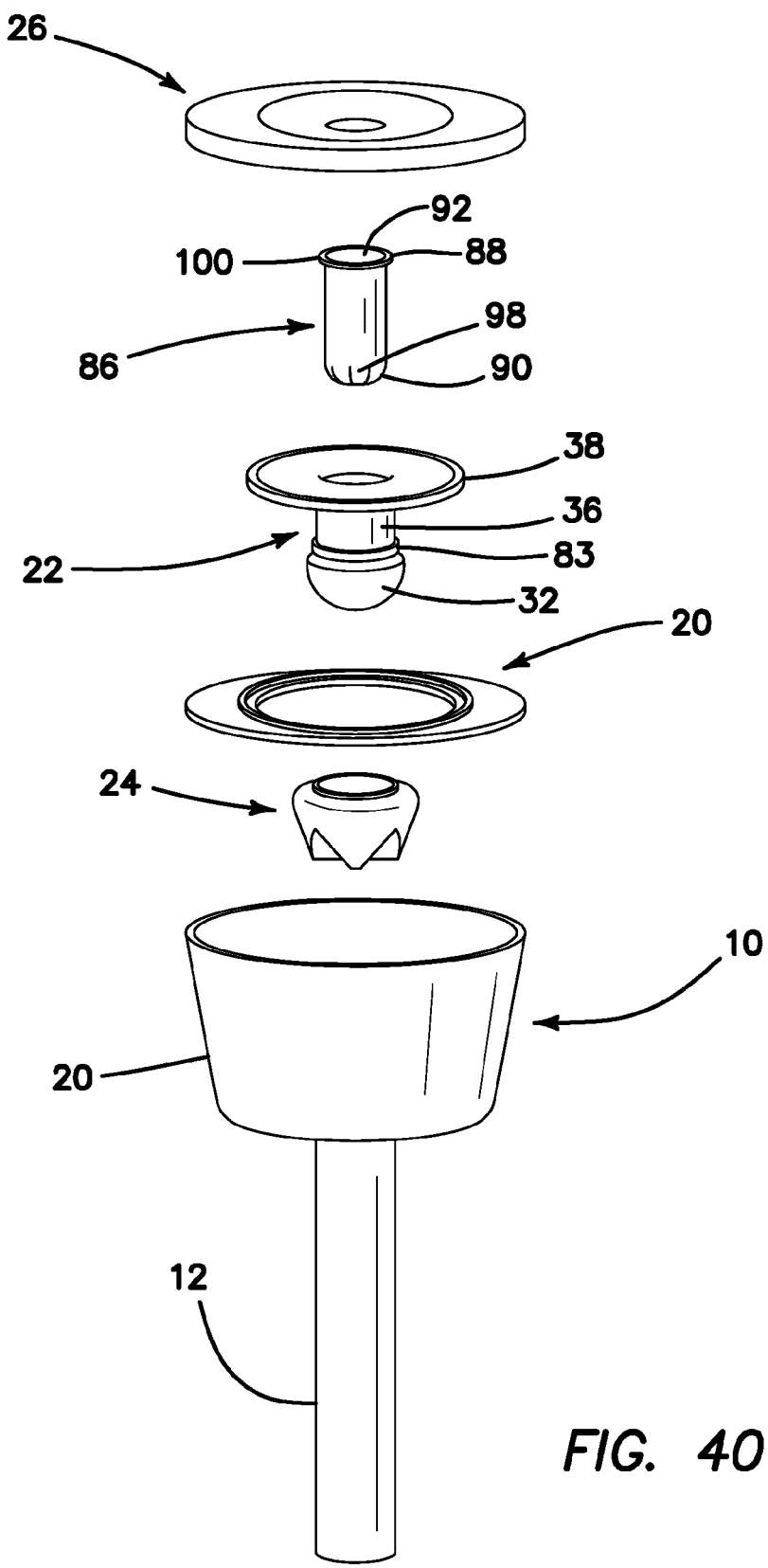
FIG. 40 is a top perspective, exploded view of a shield and a trocar assembly according to the present invention.
Figure 41:
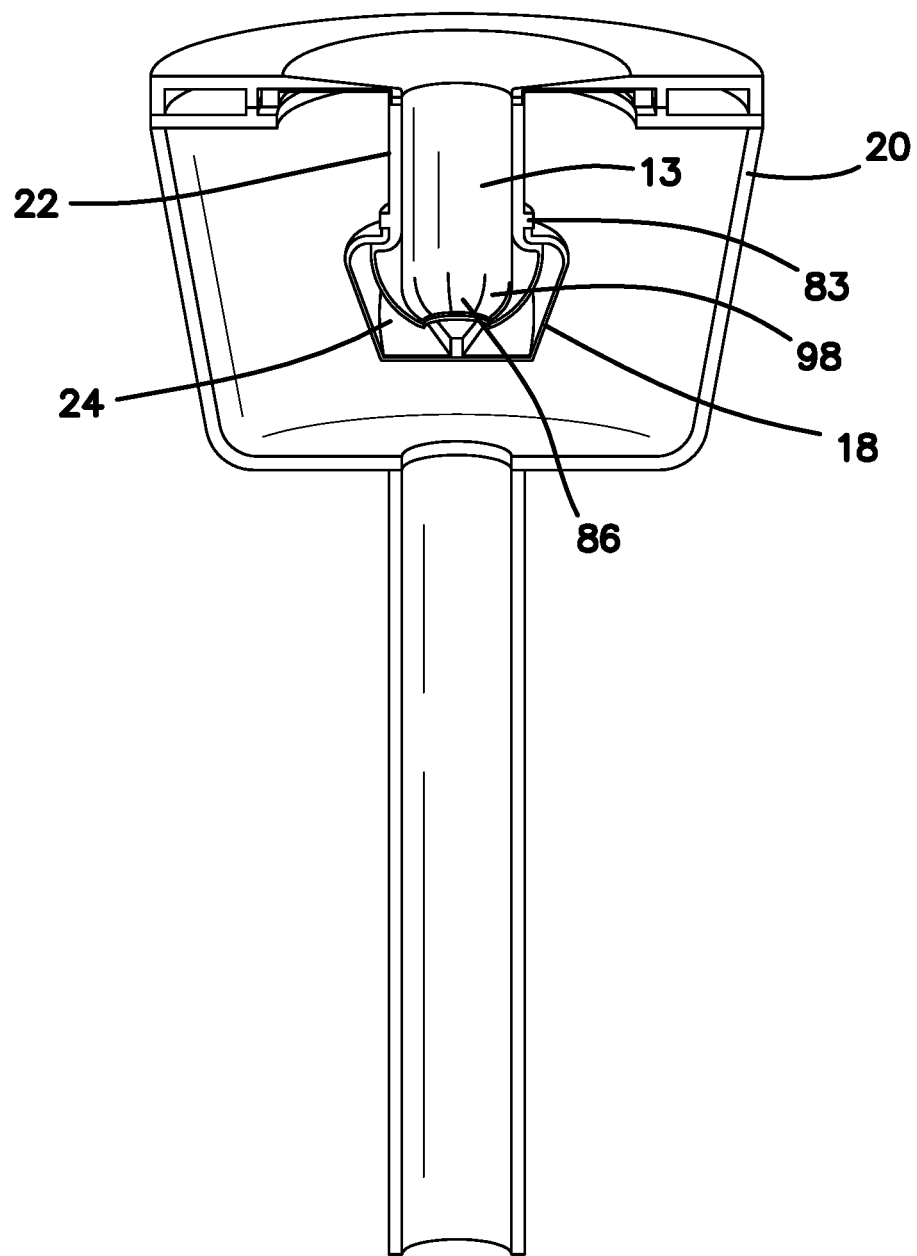
FIG. 41 is a top perspective, cross-sectional view of a shield and a trocar assembly according to the present invention.
Figure 42:
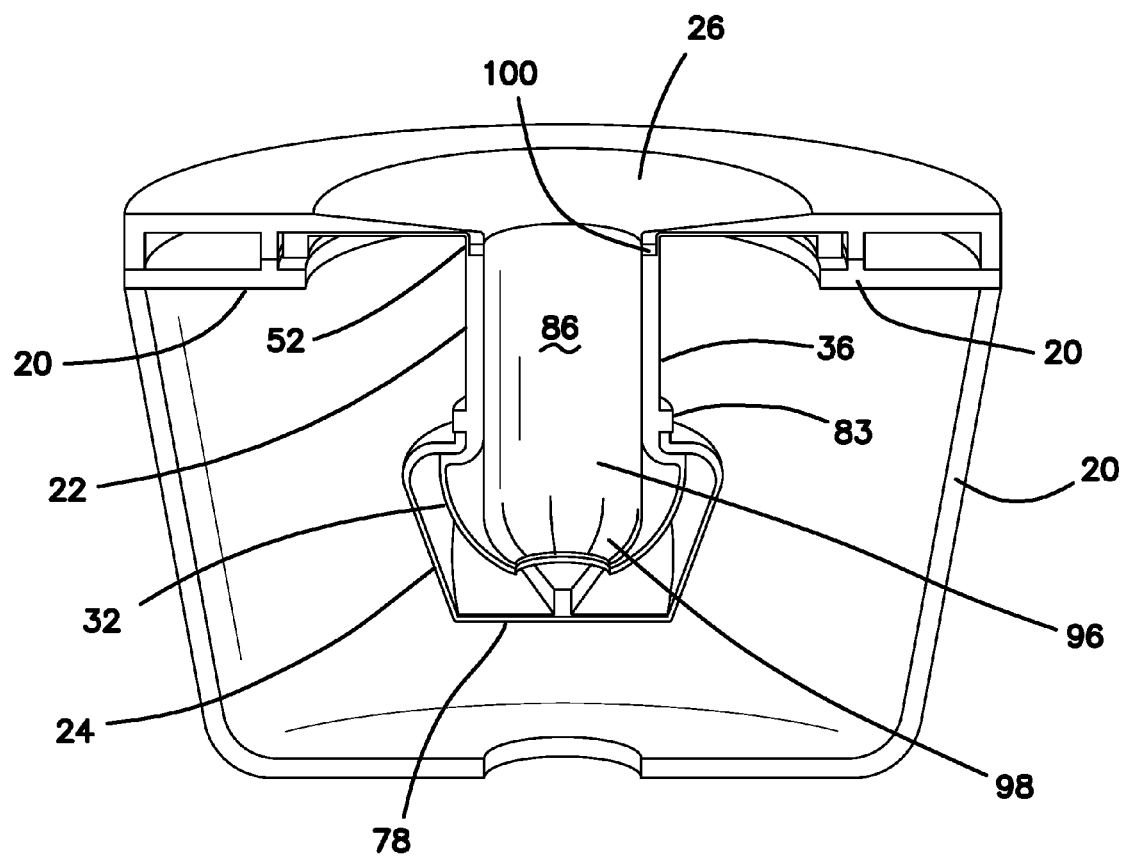
FIG. 42 is a top perspective, cross-sectional view of a shield and a trocar assembly according to the present invention.

Turning now to FIGS. 40-42, there is shown the embodiment of the zero seal 24 connected directly to the instrument seal 22 as described above with respect to FIGS. 21-33. The zero seal 24 is shown connected to the instrument seal 22 by snapping over the instrument engaging portion 32 of the instrument seal 22 and being retained between the circumferential extension 83 and the bulbous instrument engaging portion 32. This variation also includes a shield 86 located within the lumen of the instrument seal 22 as described above with respect to FIGS. 34-39 and functions in the same manner.

It is understood that various modifications may be made to the seal assembly and access device disclosed herein. Therefore, the above description should not be construed as limiting, but merely as exemplifications of preferred embodiments. Those skilled in the art will envision other modifications within the scope and spirit of the present disclosure.

We claim:

1. A surgical seal assembly for use with a surgical access device having a longitudinal axis, the seal assembly comprising:
   a seal holder including a wall portion defining a working channel dimensioned to permit passage of a surgical instrument;
   an instrument seal connected to the seal holder and disposed in the working channel; the instrument seal having a central lumen extending along a central seal axis between a proximal opening at the proximal end of the instrument seal and a distal orifice at a distal end of the instrument seal; the instrument seal comprising:
      a base portion at the proximal end of the instrument seal; the base extends laterally outwardly from the proximal opening;
      an elongate throat portion extending distally from the base portion along the seal axis; the throat portion having a throat length along the seal axis between a proximal end and a distal end of the throat portion; the central lumen having a throat inner diameter that is constant along the entire length of the throat portion from the proximal end to the distal end of the throat portion; and
      a head portion extending distally from the distal end of the throat portion; the head portion having a proximal end and a distal end; the head portion defining the distal orifice of the instrument seal at the distal end of the head portion; the distal orifice and the proximal opening being coaxial with the seal axis; the head portion having a head inner diameter that is larger than the throat inner diameter; the head inner diameter decreasing toward the distal orifice; the distal orifice having an orifice diameter that is smaller than the throat inner diameter;
   wherein the base portion is connected to the seal holder such that the throat portion pendulates together with the head portion.

2. The surgical seal assembly of claim 1 wherein the throat length is approximately twice the throat diameter.

3. The surgical seal assembly of claim 1 wherein the throat length is approximately at least twice the throat diameter.

4. The surgical seal assembly of claim 1 wherein the head portion is partially spheric.

5. A surgical seal assembly for use with a surgical access device having a longitudinal axis, the seal assembly comprising:
   a seal holder including a wall portion defining a working channel dimensioned to permit passage of a surgical instrument;
   an instrument seal connected to the seal holder and disposed in the working channel; the instrument seal having a central lumen extending along a central seal axis between a proximal opening at the proximal end of the instrument seal and a distal orifice at a distal end of the instrument seal; the instrument seal comprising:
      a base portion at the proximal end of the instrument seal; the base portion extends laterally outwardly from the proximal opening;
      an elongate throat portion extending distally from the base portion along the seal axis; the throat portion having a throat length along the seal axis between a proximal end and a distal end of the throat portion; the central lumen having a throat inner diameter that is constant along the entire length of the throat portion from the proximal end to the distal end of the throat portion; the throat length being greater than the throat diameter; and
      a head portion extending distally from the distal end of the throat portion; the head portion having a proximal end and a distal end; the head portion defining the distal orifice of the instrument seal at the distal end of the head portion; the distal orifice and the proximal opening being coaxial with the seal axis; the head portion having a head inner diameter that is larger than the throat inner diameter; the head inner diameter decreasing toward the distal orifice; the distal orifice having an orifice diameter that is smaller than the throat inner diameter.

6. The surgical seal assembly of claim 5 wherein the throat length is approximately twice the throat diameter.

7. The surgical seal assembly of claim 5 wherein the throat length is approximately at least twice the throat diameter.

8. The surgical seal assembly of claim 5 wherein the base portion is connected to the seal holder such that the throat portion pendulates together with the head portion.

9. The surgical seal assembly of claim 5 wherein the instrument engaging portion is partially spheric.

10. A surgical access port for passage through body tissue to provide access to an underlying tissue site; the surgical access port comprising:
    a working channel extending from a proximal end and a distal end; the working channel being dimensioned for receiving a surgical instrument; and a seal assembly for providing a substantial seal before, during and after insertion of a surgical instrument; the seal assembly being disposed in the working channel and including a seal holder, an instrument seal and a zero seal; the instrument seal includes a proximal base that is integrally formed and interconnected to a distal instrument engaging portion by an elongate supporting portion; the engaging portion has a diameter larger than the diameter of the supporting portion forming a mushroom-shaped head; the diameter of the engaging portion decreases toward a distal opening of the instrument seal such that the distal end of the engaging portion is substantially perpendicular to a seal axis; the supporting portion closely conforms to an inserted surgical instrument and aligns the distal opening at the distal end of the instrument engaging portion with the inserted instrument before the inserted instrument enters the instrument engaging portion from a proximal opening of the instrument seal; the proximal opening and the distal opening of the instrument seal being coaxial with the seal axis.

11. The surgical access port of claim 10 wherein the supporting portion has a length and a constant diameter along the length of the supporting portion.

12. The surgical access port of claim 10 wherein the supporting portion has a length and a diameter; the length of the supporting portion is approximately twice the diameter of the supporting portion.

13. The surgical access port of claim 10 wherein the supporting portion has a length and a diameter; the length of the supporting portion is approximately at least twice the diameter of the supporting portion.

14. The surgical access port of claim 10 wherein the instrument seal is connected at the base to seal holder such that the supporting portion and the engaging portion pendulate together relative to the seal holder.

15. The surgical access port of claim 10 wherein an inserted surgical instrument has an instrument diameter; the diameter of the supporting portion being slightly larger than the instrument diameter and the diameter of the distal opening being slightly smaller than the instrument diameter.

16. The surgical access port of claim 10 wherein an inserted surgical instrument has an instrument diameter of approximately 5.5 millimeters; the supporting portion having a length of approximately 8-14 millimeters; and the distal opening having a diameter of approximately 4.7 millimeters.

17. The surgical access port of claim 10 wherein the instrument engaging portion is partially spheric.

* * * * *